United States Patent [19]

Dean

[11] Patent Number: 4,844,727

[45] Date of Patent: Jul. 4, 1989

[54] HERBICIDAL SULFONAMIDES

[75] Inventor: Thomas R. Dean, Wilmington, Del.

[73] Assignee: E. I. Du Pont de Nemours and Company, Wilmington, Del.

[21] Appl. No.: 121,072

[22] Filed: Nov. 16, 1987

[51] Int. Cl.$^4$ .................. C07D 239/69; C07D 401/12; C07D 411/12; A01N 43/54

[52] U.S. Cl. ............................................ 71/91; 71/90; 71/92; 544/296; 544/320; 544/321; 544/323; 544/324; 544/331; 544/332

[58] Field of Search ...................... 71/90, 91; 544/296, 544/321, 324

[56] References Cited

U.S. PATENT DOCUMENTS

| | | | |
|---|---|---|---|
| 4,310,346 | 1/1982 | Levitt | 71/92 |
| 4,370,480 | 1/1983 | Levitt et al. | 71/92 |
| 4,481,029 | 11/1984 | Levitt | 71/92 |
| 4,501,607 | 2/1985 | Levitt | 71/92 |

*Primary Examiner*—John M. Ford

[57] ABSTRACT

Sulfonylureas with uniquely substituted heterocycles demonstrate activity as agricultural chemicals.

53 Claims, No Drawings

HERBICIDAL SULFONAMIDES

BACKGROUND OF THE INVENTION

Sulfonylureas with uniquely substituted heterocycles demonstrate activity as agricultural chemicals.

U.S. Pat. No. 4,383,113 and U.S. Pat. No. 4,394,506 disclose herbicidal benzenesulfonylureas of the formula

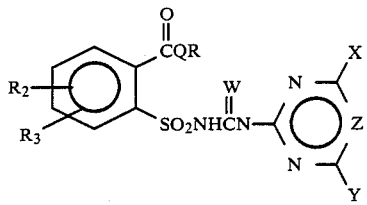

wherein

X is H, Cl, CH$_3$, OCH$_3$, OCH$_2$CH$_3$ or OCH$_2$CH$_2$OCH$_3$; and

Y, in part, is C$_1$-C$_4$ alkyl substituted with OCH$_3$, OCH$_2$CH$_3$, CN, CO$_2$CH$_3$, CO$_2$CH$_2$CH$_3$, 1 to 3 atoms of F, Cl, Br; C(O)L$^1$, SCN, ACH$_2$C(O)L, ACH(CH$_3$)C(O)L or ACH$_2$CH$_2$C(O)L.

U.S. Pat. No. 4,214,890 discloses herbicidal benzenesulfonylureas of the formula

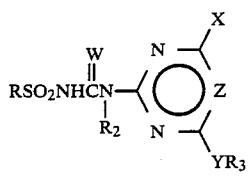

wherein

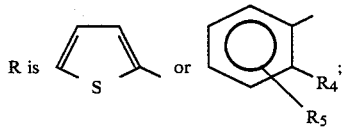

Y is O or S;

R$_3$ is CH$_2$CF$_3$, CH$_2$CH$_2$OR$_6$, CH$_2$CO$_2$R$_6$, CH(CH$_3$)CO$_2$R$_6$, —(CH$_2$)$_3$—OR$_6$ or CH$_2$CH$_2$CO$_2$R$_6$;

R$_4$ is Cl, Br, F, NO$_2$, CH$_3$, OCH$_3$, CF$_3$ or S(O)$_n$CH$_3$.

U.S. Pat. No. 4,501,607 discloses herbicidal benzenesulfonylureas of the formula

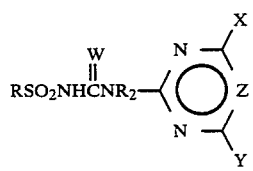

wherein

Y, in part, is C$_1$-C$_4$ alkyl substituted with OC$_2$H$_5$, CN, CO$_2$H, CO$_2$CH$_3$ or CO$_2$C$_2$H$_5$.

U.S. Pat. No. 4,544,401 and U.S. Pat. No. 4,435,206 disclose herbicidal pyridinesulfonylureas containing a heterocycle of the formula

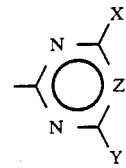

wherein

Y, in part, is H, Cl, CH$_3$, CH$_2$OR$_8$ or VR$_9$;

R$_9$, in part, is CH$_3$, CH$_2$CH$_2$OR$_8$, CH$_2$CO$_2$R$_8$ or CH(CH$_3$)CO$_2$R$_8$; and V is O or S.

U.S. Pat. No. 4,310,346 discloses herbicidal sulfonylureas of the formula

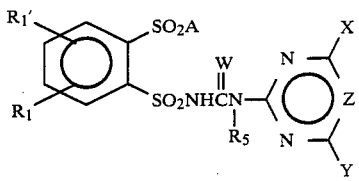

wherein

A, in part, is NR$_2$R$_3$, OCH$_2$CCl$_3$ or OCH$_2$CBr$_3$;

X is H, CH$_3$, OCH$_3$ or OCH$_2$CH$_3$;

Y, in part, is CH$_2$OCH$_3$, OCHR$_7$CO$_2$R$_{11}$, CO$_2$R$_{11}$, CH$_2$CO$_2$R$_{11}$, CH$_2$CN or CH$_2$CH$_2$CN.

U.S. Pat. No. 4,452,628 discloses herbicidal sulfonylureas of the formula

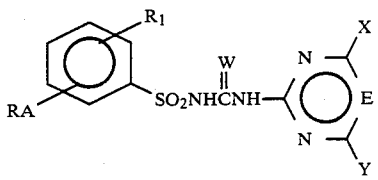

wherein

A is O of S(O)$_n$;

R is CHF$_2$, CF$_2$, CH$_2$CF$_3$ or CF$_2$CHFG; and

Y, in part, in CH$_3$, OCH$_3$, OCH$_2$CH$_2$OCH$_3$ or OCHR$^2$CO$_2$R$^3$.

U.S. Pat. No. 4,370,480 discloses *ortho*-ketone and ketal benzenesulfonylureas of the formula

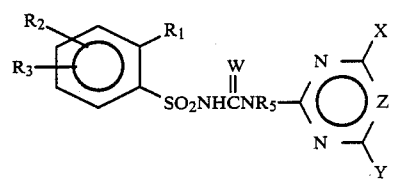

wherein

Y, in part, is C$_1$-C$_4$ alkyl substituted by OCH$_3$, OC$_2$H$_5$, CN, CO$_2$CH$_3$, CO$_2$C$_2$H$_5$ or 1 to 3 atoms of F, Cl or Br; ACH$_2$C(O)L or ACH(CH$_3$)C(O)L.

U.S. Pat. No. 4,481,029 discloses herbicidal alkoxycarbonyl sulfonylureas of the formula

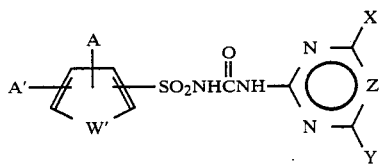
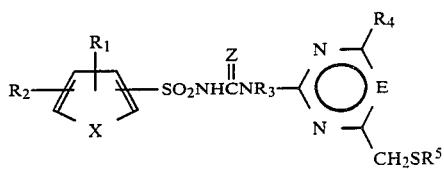

wherein

A is C(O)QR or C(T)R$^{II}$;

A' is H, Cl, Br, $C_1$–$C_4$ alkyl, $OCH_3$, $NO_2$ or $CF_3$; and

Y, in part, is $C_1$–$C_4$ alkyl substituted with $OCH_3$, $OC_2H_5$, CN, $CO_2CH_3$, $CO_2C_2H_5$, C(O)L or 1–3 atoms of F, Cl or Br; or $OCH_2C(O)L$.

U.S. Pat. No. 4,655,823 discloses herbicidal sulfonylureas of the formula

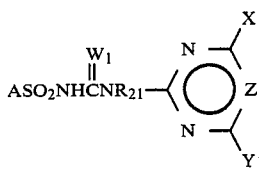

wherein

Y is $CH_2OR$, $CH_2S(O)_mR_1$, $CH(QR_1)_2m$ $CH(R_1)S(O)_mR_1$,

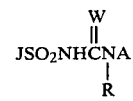

U.S. Pat. No. 4,514,211 discloses herbicidal benzofuran and benzothiophene sulfonylfureas.

SA 83/4956 discloses herbicidal sulfonylureas of the formula

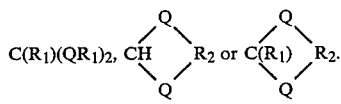

wherein

B is a single bond, $CH_2$ or $CH_2CH_2$;

$R_4$ is $C(O)R_7$; and $R_7$ is H, alkyl, haloalkyl, phenyl, halophenyl, alkylphenyl or alkoxyphenyl.

SA 84/5216 discloses herbicidal sulfonylureas of the formula

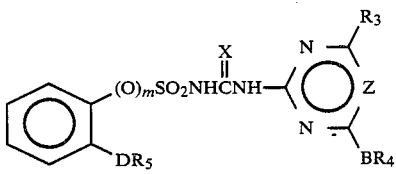

U.S. Pat. No. 4,639,264 discloses herbicidal sulfonylureas of the formula wherein $R_5$, in part, is CN, $C(Z)R^{13}$ or $P(Z)R^{14}R^{15}$.

Despite the variety of these sulfonylurea herbicides, a need still exists for additional herbicides, particularly those which are useful as post-emergent herbicides or plant growth regulators.

SUMMARY OF THE INVENTION

This invention relates to novel compounds of Formula I, agriculturally suitable compositions containing them and their method-of-use as postemergent herbicides or plant growth regulators.

$$\text{JSO}_2\text{NHCNA} \overset{W}{\underset{R}{\parallel}} \quad \text{I}$$

wherein

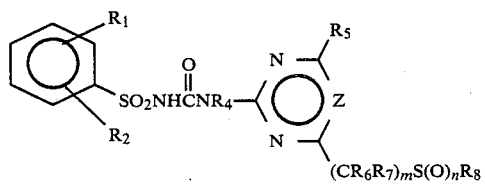

W is O or S;
R is H or $CH_3$;
$R_a$ is —CN or —$CO_2R_c$;
$R_b$ is H, $CH_3$, F, Cl, Br, $OCH_3$ or $SCH_3$;
$R_c$ is $C_1$–$C_4$ alkyl, $C_2$–$C_4$ haloalkyl, $C_3$–$C_4$ alkenyl, $C_3$–$C_4$ alkynyl or $C_2$–$C_4$ haloalkenyl;
X is H, $CH_3$, $CH_2CH_3$, $C_1$–$C_4$ alkoxy, $SCH_3$, $C_1$–$C_2$ haloalkoxy, $SCF_2H$, $CH_2OCH_3$, $NHCH_3$, $N(CH_3)_2$ or $N(OCH_3)CH_3$;
Y is O or $CH_2$;
$Y_1$ is H or $CH_3$;
Z is N or CH;
J is

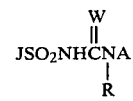

-continued

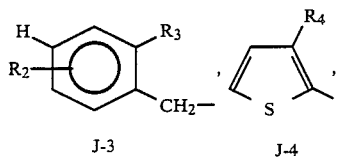

J-3, J-4

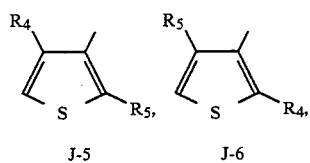

J-5, J-6

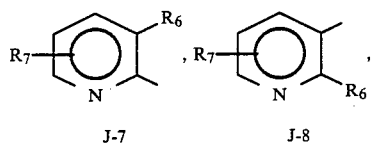

J-7, J-8

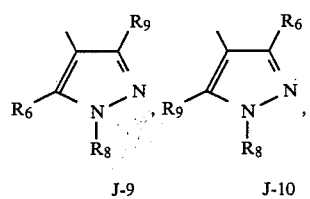

J-9, J-10

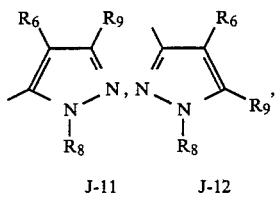

J-11, J-12

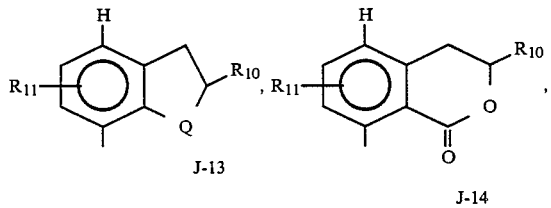

J-13, J-14

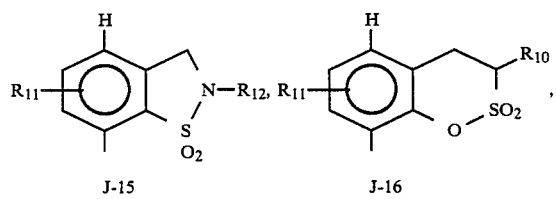

J-15, J-16

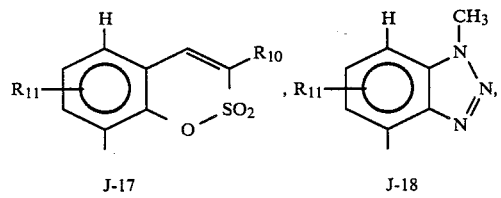

J-17, J-18

-continued

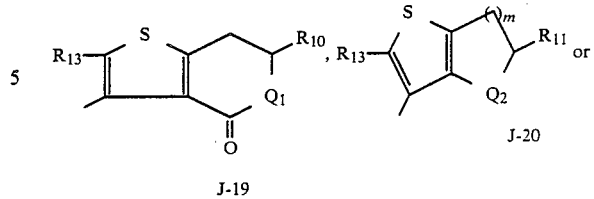

J-19, J-20

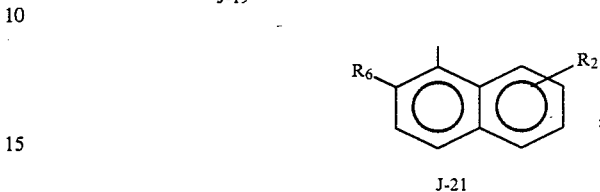

J-21

$R_1$ is $OS(O)_2R_{14}$ or L;
$R_1'$ is $C_1$-$C_3$ alkyl, $CH_2CH_2Cl$, $CH_2CH_2F$, $CH_2CF_3$ or $CH_2CH_2OCH_3$;
$R_2$ is H, Cl, Br, CN, $CH_3$, $OCH_3$, $SCH_3$, $OCH_2CF_3$, $OCF_2H$, $N(CH_3)_2$, $CH_2OCH_3$ or $CH_2SCH_3$;
$R_2'$ is H, $C_1$-$C_3$ haloalkoxy, $C_1$-$C_3$ haloalkylthio, allyloxy, propargyloxy, or $C_1$-$C_3$ alkylsulfinyl;
$R_3$ is $CO_2CH_3$, $CO_2CH_2CH_3$, $SO_2N(CH_3)_2$, $SO_2CH_3$ or $SO_2CH_2CH_3$;
$R_4$ is $SO_2NR_dR_e$, $S(O)_nR_f$ or L;
$R_5$ is H, F, Cl, Br, $SCH_3$, $OCH_3$, $CH_3$, $CO_2CH_3$ or $CO_2CH_2CH_3$;
$R_6$ is $C_1$-$C_3$ alkyl, $C_1$-$C_2$ alkoxy, $C_2$-$C_4$ haloalkenyl, F, Cl, Br, $CO_2R_g$, $C(O)NR_oR_p$, $SO_2NR_dR_e$, $S(O)_nR_f$, $C(O)R_q$, L or $CR_h(OC_1$-$C_2$ alkyl$)_2$;
$R_7$ is H, F, Cl, $CH_3$, $SCH_3$, $OCH_3$, $N(CH_3)_2$ or $CF_3$;
$R_8$ is H or $C_1$-$C_3$ alkyl;
$R_9$ is H, Cl, F, Br, $C_1$-$C_3$ alkyl or $C_1$-$C_2$ alkoxy;
$R_{10}$ is H or $CH_3$;
$R_{11}$ is H, F, Cl, Br, CN, $CH_3$, $OCH_3$, $SCH_3$ or $OCF_2H$;
$R_{12}$ is H, $C_1$-$C_4$ alkyl, $C_1$-$C_2$ haloalkyl, $CH_2OCH_3$, cyclopropyl, $C(O)CH_3$ or $CO_2CH_3$;
$R_{13}$ is H, $CH_3$, $OCH_3$, Cl, $NO_2$ or $CF_3$;
$R_{14}$ is $C_1$-$C_3$ alkyl;
$R_d$ is H, $C_1$-$C_2$ alkyl or $OCH_{13}$;
$R_e$ is $C_1$-$C_2$ alkyl;
$R_f$ is $C_1$-$C_3$ alkyl, $C_1$-$C_3$ haloalkyl, $CH_2CH=CH_2$ or $CH_2C\equiv CH$;
$R_g$ is $C_1$-$C_3$ alkyl, $CH_2CH_2Cl$, $CH_2CH_2F$ or $CH_2CF_3$;
n is 0, 1 or 2;
M is 1 or 2;
L is

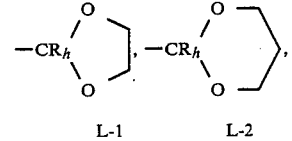

L-1, L-2

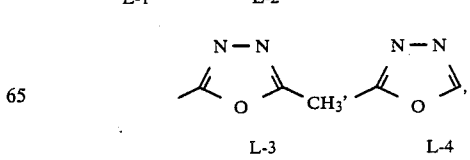

L-3, L-4

-continued

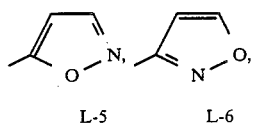
L-5, L-6

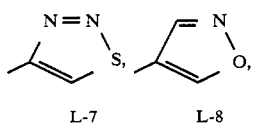
L-7, L-8

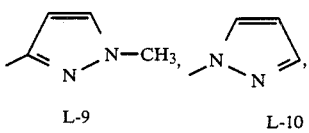
L-9, L-10

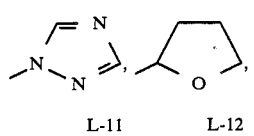
L-11, L-12

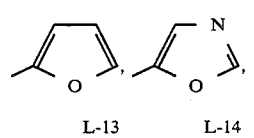
L-13, L-14

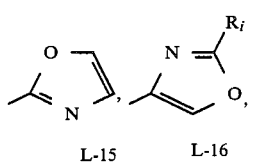
L-15, L-16

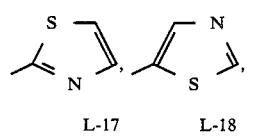
L-17, L-18

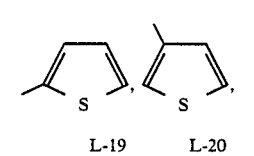
L-19, L-20

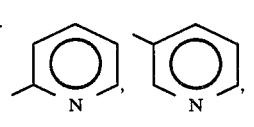
L-21, L-22

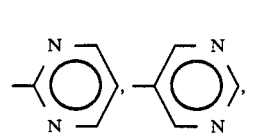
L-23, L-24

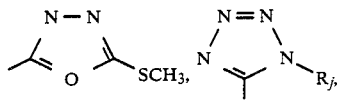
L-25, L-26

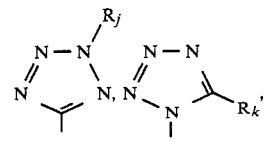
L-27, L-28

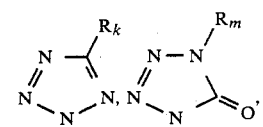
L-29, L-30

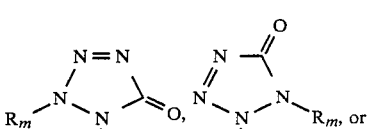
L-31, L-32, or

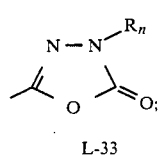
L-33

$R_h$ is H or $CH_3$;
$R_i$ is H or $CH_3$;
$R_j$ is H, $CH_3$ or $CH_2CH_3$;
$R_k$ is H, $CH_3$, $CH_2CH_3$, $OCH_3$, $OCH_2CH_3$, $SCH_3$ or $SCH_2CH_3$;
$R_m$ is H, $CH_3$ or $CH_2CH_3$;
$R_n$ is H or $CH_3$;
$R_o$ is H, $C_1$-$C_2$ alkyl or $OCH_3$;
$R_p$ is $C_1$-$C_2$ alkyl;
$R_q$ is $C_1$-$C_4$ alkyl, $C_1$-$C_4$ haloalkyl or cyclopropyl optionally substituted by halogen;
Q is O, S, SO, $SO_2$ or C(O);
$Q_1$ is O, $NCH_3$ or $NCH_2CH_3$;
$Q_2$ is S, SO or $SO_2$;
and their agricultrually suitable salts; provided that
(a) when X is $C_1$ haloalkoxy, then Z is CH;
(b) when X is $NHCH_3$, $N(CH_3)_2$ or $N(OCH_3)CH_3$, then Z is N;
(c) when J is J-1, then L is L-3 through L-33; and
(d) when $R_2'$ is H, then $R_b$ is F, Cl, Br, $OCH_3$ or $SCH_3$.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g. vinyl, 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

The term "halogen", either alone or in compound words such as "haloalkyl", denotes fluorine, chlorine, bromine or iodine. The term haloalkyl is further meant to include mono or poly substitution by the same or different halogen atoms.

PREFERRED COMPOUNDS

*Preferred* for reasons of greater ease of synthesis and/or greater herbicidal efficacy are:

(1) Compounds of *Formula I* wherein W is O.
(2) Compounds of *Preferred* 1 wherein $R_c$ is $CH_3$, $CH_2CH_3$, $C_3$-$C_4$ alkenyl or $C_3$-$C_4$ alkynyl.
(3) Compounds of *Preferred* 2 wherein Z is CH.
(4) Compounds of *Preferred* 3 wherein L is L-1, L-3, L-4, L-5, L-26, L-28 or L-30.
(5) Compounds of *Preferred* 4 wherein J is J-1;
(6) Compounds of *Preferred* 4 wherein J is J-2;
(7) Compounds of *Preferred* 4 wherein J is J-3;
(8) Compounds of *Preferred* 4 wherein J is J-4;
(9) Compounds of *Preferred* 4 wherein J is J-5;
(10) Compounds of *Preferred* 4 wherein J is J-6;
(11) Compounds of *Preferred* 4 wherein J is J-7;
(12) Compounds of *Preferred* 4 wherein J is J-8;
(13) Compounds of *Preferred* 4 wherein J is J-9;
(14) Compounds of *Preferred* 4 wherein J is J-10;
(15) Compounds of *Preferred* 4 wherein J is J-11;
(16) Compounds of *Preferred* 4 wherein J is J-12;
(17) Compounds of *Preferred* 4 wherein J is J-13;
(18) Compounds of *Preferred* 4 wherein J is J-14;
(19) Compounds of *Preferred* 4 wherein J is J-15;
(20) Compounds of *Preferred* 4 wherein J is J-16;
(21) Compounds of *Preferred* 4 wherein J is J-17;
(22) Compounds of *Preferred* 4 wherein J is J-18;
(23) Compounds of *Preferred* 4 wherein J is J-19;
(24) Compounds of *Preferred* 4 wherein J is J-20;
(25) Compounds of *Preferred* 4 wherein J is J-21;

*Specifically Preferred* for reasons of their highest herbicidal activity, greatest plant growth regulant activity and/or most favorable ease of synthesis are:

2-[[[4-(Cyanomethyl)-6-methoxypyrimidin-2-yl]aminocarbonyl]aminosulfonyl]-4-(2,2,2-trifluoroethoxy)benzoic acid, methyl ester, m.p. 155°–156° C.;

N-[[4-(Cyanomethyl)-6-methoxypyrimidin-2-yl]aminocarbonyl]-3,4-dihydro-1-oxo-1H-2-benzopyran-8-sulfonamide, m.p. 171°–176° C.;

2-[[2,3-Dihydro-2-methylbenzo[b]thiophen-7-yl)sulfonylamino]carbonylamino]-6-methoxy-4-pyrimidineacetic acid, methyl ester, S,S-dioxide, m.p. 97° C.(d).

DETAILED DESCRIPTION OF THE INVENTION

The preparation of heterocyclic sulfonylureas of Formula I can be accomplished using a wide variety of methods well known in the art. The most general methods used to prepare these materials are described below in Equations 1 to 3.

Many heterocyclic sulfonamides of Formula I can be prepared by the coupling reaction of sulfonyl isocyanates of Formula II with heterocyclic amines of Formula III as shown below in Equation 1.

EQUATION 1

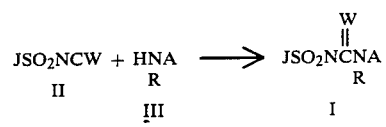

wherein

W, R, J, A and I are as previously defined.

A solution of sulfonyl isocyanate of Formula II in a suitable solvent such as methylene chloride, chloroform, dioxane, benzene, toluene, or xylene is added to the heterocyclic amine of Formula III containing a catalytic amount of a suitable base such as diazobicyclo[2.2.2]octane (DABCO) in the same solvent. The reaction is conducted at temperatures ranging from 0° C. to 80° C. and requires from 1 hr. to 48 hrs. When the reaction is complete, as judged by TLC, the product is usually isolated using one of three methods.

Often the desired product precipitates from the reaction mixture can be obtained in pure form by simple filtration. In those cases where the desired product does not precipitate from solution, the reaction mixture is concentrated and the crude product is triturated with an appropriate solvent such as 1-chlorobutane of diethyl ether and the desired product is obtained in pure form by filtration. Alternatively, pure product can be obtained by chromatography on silica gel.

Sulfonyl isocyanates of Formula II can be prepared from methods well known in the art. For a few representative examples see: U.S. Pat. No. 4,238,621; Ulrich and Sayigh, Newer Methods of Preparative Organic Chemistry, Vol. VI, pp. 223–241, Academic Press, New York and London, W. Foerst, Ed.; Japanese Patent No. 76,126,816; U.S. Pat. No. 4,394,506; and K. Kartke, Arch. Pharm., 299, 174 (1966).

Sulfonyl isocyanates of Formula II can also be generated in situ from the corresponding sulfonyl chloride in Formula IV by the action of tetraalkylammonium isocyanate salts. When this reaction is conducted in the presence of heterocyclic amines of Formula III, sulfonylureas of Formula I are produced as shown below in Equation 2.

Equation 2

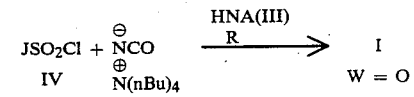

wherein:

R, J, A and I are as previously defined.

This reaction is best carried out by adding over one to six hours a solution of at least one equivalent of a tetraalkylammonium isocyanate, such as tetra-n-butylammonium isocyanate, in a suitable aprotic solvent, such as dichloromethane or tetrahydrofuran, to a mixture of sulfonyl chloride of Formula IV and heterocyclic amine of Formula III in the same solvent. The reaction is conducted at temperatures ranging from 20° C. to 40° C. When the reaction is complete, as judged by TLC, the mixture is diluted with dichloromethane, washed with 1N sulfuric acid, and dried over sodium sulfate. The mixture is concentrated to furnish the desired product of Formula I in crude form. The crude product can be purified as already described in Equation 1.

Heterocyclic sulfonamides of Formula I can be prepared by the reaction of N-substituted carbamate derivatives of sulfonamides of Formula V with heterocyclic amines of Formula III. This method as well as a general procedure for the preparation of sulfonyl carbamates is taught in U.S. Pat. No. 4,443,245.

Heterocyclic sulfonamides of Formula I can be prepared by the reaction of sulfonamides of Formula V with phenyl carbamates of Formula VI in the presence of a nonnucleophilic base. This general method is shown below (Equation 3a) and is taught in EPO Publication No. 44807. Alternatively, heterocyclic sulfonamides of Formula I can be prepared by the reaction of N-t-butyldimethyl silyl derivatives of sulfonamides of Formula V and phenyl carbamates of Formula VI in the presence of tetra-n-butyl ammonium fluoride as taught in U.S. Pat. No. 4,666,501 (Equation 3b).

Equation 3

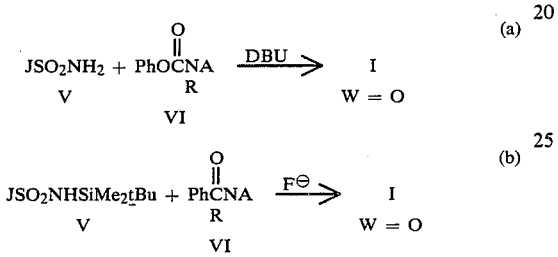

wherein:

R, J, A and I are as previously defined.

Phenyl carbamates of Formula VI can be prepared from the corresponding amines of Formula III by methods, or modifications thereof known to one skilled in the art. Some representative methods are described in South African patent application 825671 and South African patent application 825045.

Sulfonyl chlorides of Formula IV can be prepared using a variety of methods well known in the art. Some representative methods are described in: H. T. Clarke et al., Org. Synth. Coll., Vol. 1, 2nd Ed. 1941, p. 85; H. L. Yale and F. Sowinski, J. Org. Chem. 25, 1824 (1960); and H. Meerwein et al., Chem. Ber., 90. 841 (1957).

Sulfonamides of Formula V can be prepared directly from sulfonyl chlorides of Formula IV using methods well known in the art. For reviews, see F. Hawking and J. S. Lawrence, "The Sulfonamides." H. K. Lewis and Co., London, 1950 and E. H. Northey, "The Sulfonamides and Allied Compounds," Reinbold Publishing corp., New York, 1948.

There are a variety of methods in the literature for the preparation of sulfonyl chlorides of Formula IV and sulfonamides of Formula V and the following references are suggested for further details: U.S. Pat Nos. 4,169,719; 4,127,405; 4,349,506; 4,310,346; 4,435,205; 4,420,325; 4,441,910; 4,398,939; 4,481,028; 4,456,469; 4,370,479; and EPO Publication Nos. 23,422; 83,975; 13,480; and 95,925.

Heterocyclic amines of Formula III can be prepared using the procedures described in Equations 4 and 5.

Heterocyclic amines of Formula III can be prepared from the corresponding haloheterocyclic amine of Formula VI via the scheme shown in Equation 4. The halogen group in heterocyclic amines of Formula VI is displaced by activated enolate derivatives of Formula VII to furnish the substitution product of Formula VIII. The t-butyl ester moiety of compounds of Formula VIII can then be decarboxylated under mildly acidic conditions to furnish heterocyclic amines of Formula III.

Equation 4

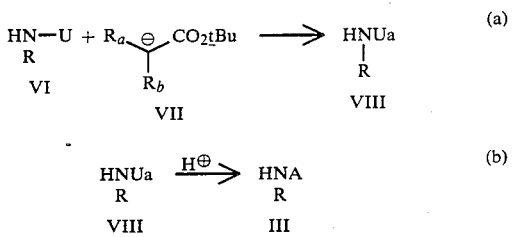

wherein:

$R$, $R_a$, $R_c$ and A are as previously defined and $R_b$ is H, $CH_3$, F, $SCH_3$ or $OCH_3$, and U is

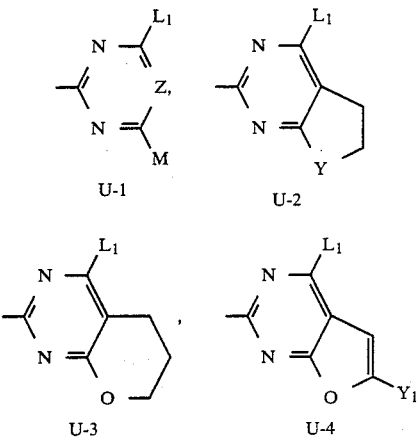

$L_1$ is Cl, Br of I;

M is X or $L_1$;

Z, $Y_1$, Y, and X are as previously defined; and $U_a$ is

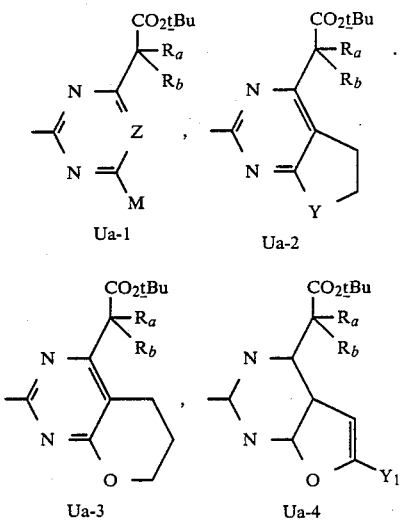

M is $L_1$, or X, $R_b$ is H, $CH_3$, F, $SCH_3$ or $OCH_3$; and $R_a$, $R_c$, X, $Y_1$, Y, and Z are as previously defined.

The reaction is best carried out by adding active methylene compounds of Formula VIII (which are well known in the art) to a suitable base such as sodium or patassium hydride in a polar aprotic solvent such as N,N-dimethylformamide at temperatures ranging from 0° C. to 15° C. for reaction times of 1 to 8 hours. When the formation of the anion is complete, the haloheterocyclic amine of Formula VI is added either batchwise or in a suitable solvent such as N,N-dimethylformamide. The mixture is allowed to stirr at temperatures ranging from 25° C. to 120° C. for reaction times of 1 to 48 hours. When the reaction is complete, as judged by TLC, the mixture is poured onto a mixture of ice and water and acidified to pH 3-4 using concentrated HCl. In some cases, the product precipitates from solution upon acidification and in these cases, simple filtration furnishes pure heterocyclic amines of Formula VIII. In those cases where the product does not precipitate it is isolated by extraction into ethyl acetate or diethyl ether. Pure heterocyclic amines of Formula VIII can be obtained by column chromatography on silica gel.

The conversion of heterocyclic amines of Formula VIII to the desired heterocycles of Formula III is best carried out by adding the heterocylcic amine of Formula VIII to a solution of an appropriate acid such as trifluoroacetic acid or p-toluenesulfonic acid in an inert solvent such as methylene chloride or benzene at temperatures ranging from 0° C. to 80° C. The reaction is allowed to proceed for from 1 to 48 hours. When the reaction is complete as judge by TLC the mixture is cooled and in some cases the pure heterocyclic amines of Formula III are collected by filtration. In other cases, the reaction mixture is concentrated and the reaction mixture is neutralized using aqueous sodium bicarbonate and the desired product is extracted into an appropriate solvent such as ethyl acetate. The organic layer is dried over sodium sulfate and concentrated to furnish the crude product. Heterocyclic amines of Formula III can be obtained in pure form either by trituration with a suitable solvent such as 1-chlorobutane or diethyl ether or by column chromatography on silica gel.

Alternatively, for heterocyclic amines of Formula VIIIa the t-butyl ester group can be removed by the action of chlorotrimethylsilane and sodium iodide in hot acetonitrile as shown in Equation 5.

Equation 5

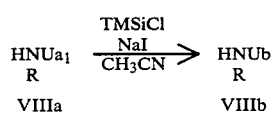

wherein:
R is previously defined and
$Ua_1$ is

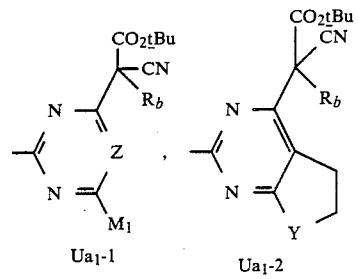

Ub is

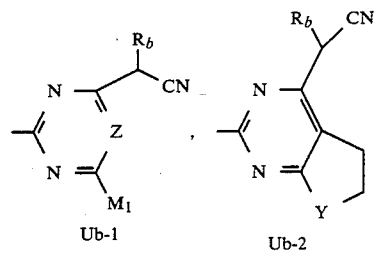

wherein:
$R_b$ is H, CH$_3$, F, or SCH$_3$ and Y=CH$_2$;
$M_1$ is Cl, Br, I, H, CH$_3$, CH$_2$CH$_3$, or SCH$_3$; and
Z is as previously defined.

This is best done by adding an excess of chlorotrimethylsilane to a stirring solution of the hetetocyclic amine of Formula III containing from a catalytic amount up to a full equivalent of sodium iodide. The mixture is stirred at temperatures ranging from 0° C. to 82° C. for reaction times of 1 hour to 48 hours. When the reaction is complete as judged by TLC, the mixture is filtered and the filtrate is dissolved in a suitable solvent such as ethyl acetate and washed with water and brine and dried. Pure heterocyclic amines of Formula VIII are then obtained by trituration of chromatography as described above in Equation 4.

Those heterocyclic amines of Formula III where $R_b$ is other than hydrogen or methoxy can be prepared from the intermediate heterocyclic amines of Formula VIII (where $R_b$ is hydrogen). In those cases the intermediate amine of Formula VIII is first deprotonated with base and subsequently treated with an appropriate electrophile to yield, after treatment with mild acid, the desired substituted heterocyclic amines of Formula III (Equation 6).

Equation 6

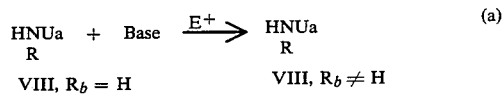

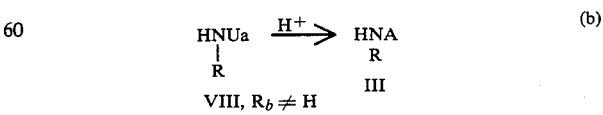

wherein:
M is $L_1$ or X, and Rb is H, CH$_3$, Cl, Br or SCH$_3$;
E+ is CH$_3$I, Cl$_2$, Br$_2$, CH$_3$—S—SCH$_3$ or ClSCH$_3$; and $R_1$, $R_a$, $R_c$, $L_1$, X, Ua and A are as previously defined.

This reaction is best carried out by adding the heterocyclic amine of Formula VIII (where $R_b$ is hydrogen) in an appropriate solvent such as N,N-dimethylformamide, dimethylsufloxide or tetrahydrofuran to a suitable base such as sodium or potassium hydride, potassium t-butoxide, or sodium methoxide in the same solvent at a temperature ranging from 0° C. to 50° C. for from 1 to 48 hours. To the anion is added dropwise the appropriate electrophile either in the same solvent or neat at a temperature ranging from 0° C. to 50° C. for 1 to 48 hours and the reaction is allowed to proceed until it is deemed complete as judged by TLC. The reaction mixture is poured onto ice water and the product is isolated by filtration if it is a solid or by extraction into an appropriate solvent such as ethyl acetate or diethyl ether. Heterocycles of Formula VIII can then be isolated in pure from by trituration or column chromatography on silica gel in the same general manner described in Equation 1. The procedure for cleaving the t-butyl ester group in these compounds is the same as described above in Equation 4.

Heterocyclic amines of Formula III where A is A-1 can be prepared from the heterocyclic amines in Formula VIII where Ub is Ub-1 and $L_1$ is Cl, Br or I. For these compounds the heterocyclic amine of Formula VIII is treated with the appropriate alkoxide or mercaptide ion using methods well known in the art. For a review of the synthesis of 2-aminopyrimidines see "The Chemistry of Heterocyclic Compounds", Vol. 16, John Wiley and Sons, New York (1962). For similar reviews of the synthesis of 2-amino-s-triazines see "The Chemistry of Heterocyclic Compounds", Vol. 13, John Wiley, New York, 1959, F. C. Schaefer, U.S. Pat. No. 3,154,547 and F. C. Schaefer and K. R. Huffman, J. Org. Chem., 38, 1812 (1963).

Heterocyclic amines of Formula VI where U is U-2, U-3 and U-4 are known and two useful references are U.S. Pat. Nos. 4,339,267 and 4,487,626.

A number of other general methods known to be useful for the preparation of heterocyclic amines of Formula III can be found in Katritzky and Rees, "Comprehensive Heterocyclic Chemistry", Vol. 3, Pergamon Press Ltd., New York, 1984.

EXAMPLE 1

2-amino-4-chloro-6-cyano-pyrimidylacetate-t-butyl ester

To a suspension of sodium hydride (17.6 g, 733 mmol) in dry N,N-dimethylformamide (DMF) at 0° C. was added dropwise t-butyl cyanoacetate (96 g, 680 mmol). The tan suspension was stirred at 0° C. for 0.5 hours then 2-amino-4,6-dichloropyrimidine (58.7 g, 358 mmol) was added batchwise. The mixture was heated slowly to 90° C. and the reaction was held at 90° C. for 18 hours. The reaction mixture was poured onto water (1 l) and the mixture was filtered. The filtrate was acidified with con HCl to pH 6 and the resultant solid was filtered and washed with water and hexanes and dried to furnish 99.64 g of the desired subject as a green powder, m.p. 107°–109° C. NMR (200 mHz) D6-acetone δ 12.8 (bs, 1 H), 8.0 (bs, 1 H), 7.8 (bs, 1 H), 6.3 (s, 1 H), 1.5 (s, 9 H).

EXAMPLE 2

2-amino-4-chloro-6-pyrimidylacetonitrile 2-amino-4-chloro-6-cyano-pyrimidylacetate-t-butyl ester (100 g, 372.5 mmol) was suspended in dry acetonitrile (1.2 l) containing sodium iodide (55.84 g, 372.5 mmol) and warmed to 40° C. until the mixture became homogeneous. Then chlorotrimethylsilane (200 ml) was added and the orange suspension was heated at reflux. After 1 hour, TLC analysis (elute with 1:1 ethyl acetate/hexanes) indicated a complete reaction and the reaction was filtered and the filtrate was concentrated. The residue was diluted with ethyl acetate and washed with water and sodium bicarbonate solution and dried with magnesium sulfate. The crude product was slurried in activated carbon, filtered and concentrated to give 38.46 g of a green solid. This was again dissolved in ethyl acetate and passed through a 4-inch pad of silica gel and then concentrated to give the desired subject as a green solid, m.p. 110°–115° C. NMR (200 mHz) D6-acetone δ 6.8 (s, 1 H), 6.8–6.6 (bs, 1 H), 3.95 (s, 2 H).

EXAMPLE 3

2-amino-4-methoxy-6-pyrimidylacetonitrile 2-amino-4-chloro-6-pyrimidylacetonitrile (31.6 g, 204.6 mmol) was dissolved in methanol (500 ml) and then sodium methoxide in methanol (46.8 ml, 204.6 mmol) was added at 25° C. The resultant dark solution was heated at reflux for 1 hour and after this time TLC indicated complete reaction. The reaction was cooled and acidified to pH 6 with acetic acid and the mixture was filtered. The filtrated was concentrated and the residue was taken up in ethyl acetate and washed with water and brine and dried with magnesium sulfate. The brown solid was chromatographed on silica gel using 1:1 ethyl acetate/hexane as eluent to furnish two fractions. Fraction A furnished 6.9 g of pure subject as a yellow solid, m.p. 117°–118° C. Fraction B furnished 4.23 g of impure subject as a pink solid, m.p. 95°–98° C. NMR (fraction A) (90 mHz) D6-acetone δ 6.2–5.9 (bs, 2 H), 6.1 (s, 1 H), 3.9 (s, 3 H), 3.7 (s, 2 H).

EXAMPLE 4

Benzo(B)thiophene-7-sulfonamide, N-((4-(cyanomethyl)-6-methoxy-pyrimidin-2-yl)aminocarbonyl)-2,3-dihydro-2-methyl-, 1,1-dioxide Benzo(B)thiophene-7-sulfonylisocyanate-2,3-dihydro-2-methyl-, 1,1-dioxide in nitrobenzene and xylenes (10 ml @ 10% or 0.88 g, 3.06 mmol) was added to 2-amino-4-methoxy-6-pyrimidylacetonitrile in methylene chloride (c.a. 5 ml) containing a catalytic amount of DABCO. The mixture was allowed to stir at 25° C. until all the heterocycle had been consumed. The mixture was filtered and the filtrate was dissolved in ethyl acetate and washed with 5% sodium bicarbonate solution. The bicarbonate washes were acidified with 1 N HCl and the desired subject was collected as a white solid, m.p. 200°–205° C. NMR (200 mHz) D6-acetone δ 12.9 (bs, 1 H), 9.6 (bs, 1 H), 7.7–8.3 (m, 3 H), 6.7 (s, 1 H), 4.1 (bs, 5 H), 3.7 (m, 2 H) 3.1 (m, 1 H), 1.4 (d, 3 H).

Using the methods taught in Equations 1–6, methods (or modifications thereof) referred to by reference and Examples 1 to 4, one skilled in the art can prepare the following compounds of Tables 1 to 19.

TABLE I

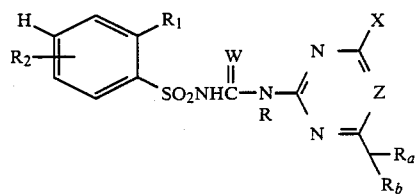

| R | W | R2 | R1 | Z | X | Ra | Rb | (m.p. °C.) |
|---|---|---|---|---|---|---|---|---|
| CH3 | O | H | L-1,Rh=H | CH | OCH3 | CN | H | |
| H | S | H | L-1,Rh=H | CH | OCH3 | CN | H | |
| H | O | H | L-1,Rh=CH3 | CH | OCH3 | CN | H | |
| H | O | H | L-1,Rh=CH3 | CH | OCH3 | CN | H | |
| H | O | H | L-1,Rh=CH3 | CH | OCH3 | CN | F | |
| H | O | H | L-1,Rh=CH3 | CH | OCH3 | CN | OCH3 | |
| H | O | H | L-1,Rh=CH3 | N | OCH3 | CN | H | |
| H | O | H | L-1,Rh=CH3 | CH | OCH3 | CO2CH3 | F | |
| H | O | H | L-1,Rh=CH3 | CH | OCH3 | CO2CH3 | OCH3 | |
| H | O | H | L-3 | CH | OCH3 | CN | H | |
| H | O | H | L-4 | N | OCH3 | CO2CH3 | F | |
| H | O | H | L-5 | CH | OCH3 | CN | F | |
| H | O | H | L-26,Rj=CH3 | CH | OCH3 | CN | H | |
| H | O | H | L-26,Rj=CH3 | CH | OCH3 | CO2CH3 | H | 185–186 |
| H | O | H | L-28,Rk=CH3 | CH | OEt | CN | OCH3 | |
| H | O | H | L-30,Rm=CH3 | N | OEt | CO2CH3 | F | |
| H | O | H | OS(O)2CH2CH3 | CH | OCH3 | CN | H | 88–93 (d) |

TABLE II

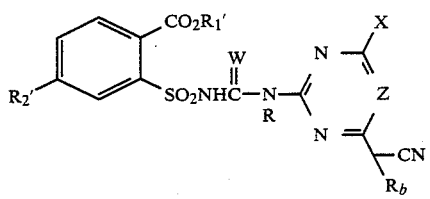

| R | W | R2' | R1' | Z | X | Rb | (m.p. °C.) |
|---|---|---|---|---|---|---|---|
| CH3 | O | OCF2H | CH3 | CH | OCH3 | H | |
| H | O | OCF2H | CH2CH3 | CH | OCH3 | H | 137–139 |
| H | S | OCF2H | CH3 | CH | OCH3 | H | |
| H | O | OCH2CF3 | CH3 | CH | OCH3 | H | |
| H | O | OCH2CF3 | CH3 | CH | OCH3 | H | 155–156 |
| H | O | OCH2CF3 | CH3 | N | OCH3 | H | |
| H | O | SCF2H | CH3 | CH | OCH3 | H | |
| H | O | SCH2CF3 | CH3 | N | OCH3 | H | |
| H | O | SCH2CF3 | CH3 | N | OCH3 | H | |
| H | O | SCH2CF3 | CH3 | CH | OEt | H | |
| H | O | OCH2CHCH2 | CH3 | CH | OCH3 | F | |
| H | O | OCH2CHCH2 | CH3 | CH | OCH3 | OCH3 | |
| H | O | OCH2CF3 | CH3 | N | OCH3 | SCH3 | |
| H | O | OCH2CF3 | CH2CH3 | CH | OCH3 | Cl | |
| H | O | OCH2CF3 | CH3 | CH | OCH3 | CH3 | |
| H | O | OCF2H | CH3 | CH | CH3 | OCH3 | |
| H | O | OCF2H | CH3 | CH | CH2CH3 | H | |
| H | O | OCF2H | CH3 | N | CH3 | F | |
| H | O | S(O)CH3 | CH2CH2CH3 | CH | OCH3 | H | |
| H | O | S(O)CH3 | CH2CH2Cl | CH | OCH3 | F | |
| H | O | S(O)CH3 | CH2CH2OCH3 | CH | OCH3 | H | |
| H | O | S(O)Et | CH3 | CH | OEt | H | |
| H | O | S(O)CH3 | CH3 | N | N(CH3)2 | H | |
| H | O | S(O)Pr | CH3 | CH | OCH3 | H | |
| H | O | OCH2CCH | CH3 | CH | OCH3 | H | |
| H | O | S(O)CH3 | CH3 | CH | SCH3 | H | |
| H | O | S(O)CH3 | CH3 | CH | OCF2H | H | |
| H | O | S(O)CH3 | CH3 | CH | SCF2H | H | |
| H | O | S(O)CH3 | CH3 | N | NHCH3 | H | |
| H | O | S(O)CH3 | CH3 | N | N(OCH3)CH3 | H | |
| H | O | S(O)CH3 | CH3 | CH | H | H | |
| H | O | S(O)CH3 | CH3 | CH | CH2OCH3 | H | |
| H | O | S(O)CH3 | CH3 | CH | OCH2CF3 | H | |
| H | O | S(O)CH3 | CH3 | N | OCH3 | Br | |
| H | O | S(O)CH3 | CH3 | CH | OCH3 | CH3 | |

TABLE III

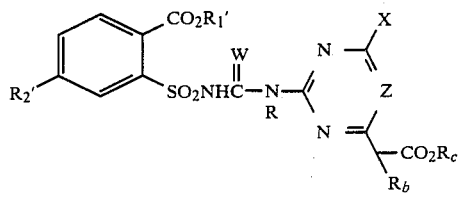

| R | W | R2' | R1' | Z | X | Rb | Rc | (m.p. °C.) |
|---|---|---|---|---|---|---|---|---|
| CH3 | O | OCF2N | CH3 | CH | OCH3 | H | CH2CH3 | |
| H | O | OCF2H | CH2CH3 | CH | OCH3 | H | CH3 | 110–112 |
| H | S | OCF2H | CH3 | CH | OCH3 | H | (CH2)2CH3 | |
| H | O | OCH2CF3 | CH3 | CH | OCH3 | H | CH3 | 105–108 |
| H | O | OCH2CF3 | CH2CH3 | CH | OCH3 | H | CH2CH2Cl | |
| H | O | OCH2CF3 | CH3 | N | OCH3 | H | CH2CF3 | |
| H | O | SCF2H | CH3 | CH | OCH3 | H | CH2(CH2)2Cl | |
| H | O | SCF2H | CH3 | N | OCH3 | H | CH2CHCH2 | |
| H | O | SCH2CF3 | CH3 | N | OCH3 | H | CH2CHCHCH3 | |
| H | O | SCH2CF3 | CH3 | CH | OEt | H | CH2CCH | |
| H | O | OCH2CHCH2 | CH3 | CH | CH3 | F | CH2CCCH3 | |
| H | O | OCH2CHCH2 | CH3 | CH | CH3 | OCH3 | CH2C(Cl)CH2 | |
| H | O | OCH2CF3 | CH3 | N | OCH3 | SCH3 | CH2C(Br)CH2 | |
| H | O | OCH2CF3 | CH2CH3 | CH | OCH3 | Cl | CH3 | |
| H | O | OCH2CF3 | CH3 | CH | OCH3 | CH3 | CH3 | |
| H | O | OCF2H | CH3 | CH | CH3 | OCH3 | CH2CH3 | |
| H | O | OCF2H | CH3 | CH | CH2CH3 | H | CH2CH3 | |
| H | O | OCF2H | CH3 | N | CH3 | F | CH2CH3 | |
| H | O | S(O)CH3 | CH3 | CH | OCH3 | F | CH3 | |
| H | O | S(O)CH3 | CH2CH2CH3 | CH | OCH3 | H | CH3 | |
| H | O | S(O)CH3 | CH2CH2Cl | CH | OCH3 | F | CH3 | |
| H | O | S(O)CH3 | CH2CH2OCH3 | CH | OCH3 | H | CH3 | |
| H | O | S(O)Et | CH3 | CH | OEt | H | CH(CH3)2 | |
| H | O | S(O)CH3 | CH3 | N | N(CH3)2 | H | CH(CH3)2 | |
| H | O | S(O)Pr | CH3 | CH | OCH3 | H | CH(CH3)2 | |
| H | O | OCH2CCH | CH3 | CH | OCH3 | H | CH(CH3)2 | |
| H | O | S(O)CH3 | CH3 | CH | SCH3 | H | CH(CH3)2 | |
| H | O | S(O)CH3 | CH3 | CH | OCF2H | H | CH(CH3)2 | |
| H | O | S(O)CH3 | CH3 | CH | SCF2H | H | CH(CH3)2 | |
| H | O | S(O)CH3 | CH3 | N | NHCH3 | H | CH(CH3)2 | |
| H | O | S(O)CH3 | CH3 | N | N(OCH3)CH3 | H | CH3 | |
| H | O | S(O)CH3 | CH3 | CH | H | H | CH3 | |
| H | O | S(O)CH3 | CH3 | CH | CH2OCH3 | H | CH3 | |
| H | O | S(O)CH3 | CH3 | CH | OCH2CF3 | H | CH3 | |
| H | O | S(O)CH3 | CH3 | N | OCH3 | Br | CH3 | |
| H | O | S(O)CH3 | CH3 | CH | OCH3 | CH3 | CH3 | |

TABLE IV

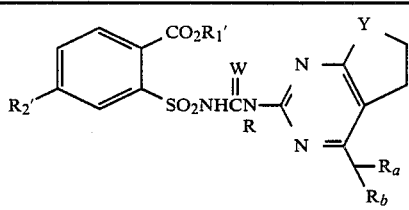

| R | W | R2' | R1' | Y | Ra | Rb | (m.p. °C.) |
|---|---|---|---|---|---|---|---|
| H | O | OCF2H | CH3 | O | CN | H | |
| CH3 | O | OCF2H | CH3 | O | CN | H | |
| H | S | OCF2H | CH3 | O | CN | H | |
| H | O | OCH2CF3 | CH3 | O | CN | F | |
| H | O | OCH2CF3 | CH3 | O | CN | OCH3 | |
| H | O | S(O)CH3 | CH3 | O | CN | SCH3 | |
| H | O | S(O)CH3 | CH3 | O | CN | Cl | |
| H | O | S(O)CH3 | CH3 | O | CN | CH3 | |
| H | O | OCF2H | CH3 | CH2 | CN | H | |
| H | O | OCF2H | CH3 | O | CO2CH3 | H | |
| H | O | OCF2CF3 | CH3 | O | CO2CH2CH3 | F | |
| H | O | OCH2CF3 | CH3 | O | CO2CH2CH2Cl | F | |
| H | O | OCH2CF3 | CH3 | O | CO2CH2CH3 | OCH3 | |

TABLE V

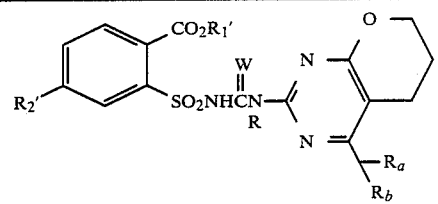

| R | W | R2' | R1' | Ra | Rb | (m.p. °C.) |
|---|---|---|---|---|---|---|
| H | S | S(O)CH3 | CH3 | CN | H | |
| CH3 | O | S(O)CH3 | CH3 | CN | H | |
| H | O | OCF2H | CH2CH3 | CN | F | |
| H | O | OCF2H | CH3 | CN | OCH3 | |
| H | O | OCF2H | CH3 | CN | SCH3 | |
| H | O | S(O)CH3 | CH3 | CO2CH3 | H | |
| H | O | S(O)CH3 | CH3 | CO2CH2CH3 | F | |
| H | O | S(O)CH3 | CH3 | CO2CH3 | OCH3 | |
| H | O | OCH2CF3 | CH3 | CO2CH3 | CH3 | |
| H | O | OCF2H | CH2CH3 | CO2CH3 | H | |
| H | O | OCF2H | CH3 | CO2CH3 | SCH3 | |
| H | O | OCF2H | CH3 | CO2CH3 | Cl | |

TABLE VI

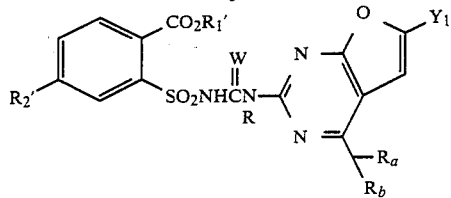

| R | W | R2' | R1' | Y1 | Ra | Rb | (m.p. °C.) |
|---|---|---|---|---|---|---|---|
| H | S | S(O)CH3 | CH3 | H | CN | H | |
| CH3 | O | S(O)CH3 | CH3 | CH3 | CN | H | |
| H | O | OCF2H | CH2CH3 | CH3 | CN | F | |
| H | O | OCF2H | CH3 | H | CN | OCH3 | |
| H | O | OCF2H | CH3 | H | CN | SCH3 | |
| H | O | S(O)CH3 | CH3 | CH3 | CO2CH3 | H | |
| H | O | S(O)CH3 | CH3 | CH3 | CO2CH2CH3 | F | |
| H | O | S(O)CH3 | CH3 | H | CO2CH3 | OCH3 | |
| H | O | OCH2CF3 | CH3 | H | CO2CH3 | CH3 | |
| H | O | OCF2H | CH2CH3 | CH3 | CO2CH3 | H | |
| H | O | OCF2H | CH3 | CH3 | CO2CH3 | SCH3 | |
| H | O | OCF2H | CH3 | CH3 | CO2CH3 | Cl | |

TABLE VII

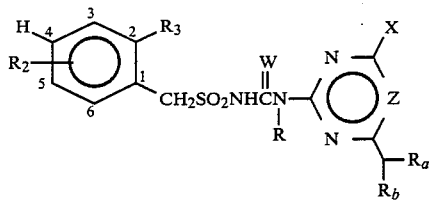

| R | W | R2 | R3 | Z | X | Ra | Rb | (m.p. °C.) |
|---|---|---|---|---|---|---|---|---|
| H | S | H | CO2CH3 | CH | OCH3 | CN | H | |
| CH3 | O | H | CO2CH3 | CH | OCH3 | CN | H | |
| H | O | H | CO2CH3 | CH | OCH3 | CN | F | |
| H | O | 5-CH3 | CO2CH3 | CH | OCH3 | CN | H | |
| H | O | 5-F | CO2CH3 | N | OCH3 | CN | CH3 | |
| H | O | H | CO2CH2CH3 | CH | OCH3 | CN | H | |
| H | O | 5-SCH3 | CO2CH3 | N | OCH3 | CN | OCH3 | |
| H | O | 5-OCF2H | CO2CH3 | CH | OCH3 | CN | SCH3 | |
| H | O | H | CO2CH3 | CH | OCH3 | CO2CH3 | F | |
| H | O | H | CO2CH3 | N | OCH3 | CO2CH3 | H | |
| H | O | H | CO2CH3 | N | OCH3 | CO2CH2CH3 | OCH3 | |
| H | O | 5-Cl | CO2CH3 | CH | OCH3 | CO2CH3 | SCH3 | |
| H | O | 5-CH3 | CO2CH3 | CH | OCH2CH3 | CO2CH3 | CH3 | |

TABLE VIII

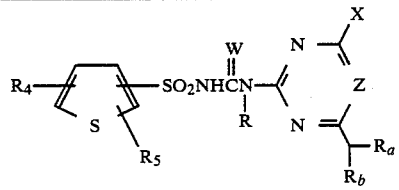

| R | W | Bridge | R4 | R5 | Z | X | Ra | Rb | (m.p. °C.) |
|---|---|---|---|---|---|---|---|---|---|
| CH3 | O | 3- | 1-SO2N(CH3)2 | H | CH | OCH3 | CN | H | |
| H | S | 3- | 1-SO2N(CH3)2 | H | CH | OCH3 | CN | H | |
| H | O | 3- | 4-SO2N(CH3)2 | H | CH | OCH3 | CN | F | |
| H | O | 3- | 2-SO2CH2CH3 | H | CH | OCH3 | CN | H | |
| H | O | 3- | 2-SO2CH2CH3 | 4-CH3 | CH | OCH3 | CN | H | |
| H | O | 2- | 3-SO2CH2CH3 | H | CH | OCH3 | CN | OCH3 | |
| H | O | 2- | 3-SO2N(CH3)2 | H | N | OCH3 | CN | F | |
| H | O | 2- | 3-SCH2CH3 | H | CH | OCH3 | CN | SCH3 | |
| H | O | 3- | 4-SO2CH2CH3 | H | CH | OCH3 | CO2CH3 | H | |
| H | O | 3- | 2-SCH2CH3 | 4-CO2CH3 | CH | OCH3 | CO2CH3 | F | |
| H | O | 3- | 2-CO2CH3 | 4-CH3 | CH | OCH3 | CO2CH3 | CH3 | |
| H | O | 3- | 2-SO2CH2CH3 | 4-Br | N | OCH3 | CO2CH3 | SCH3 | |

TABLE VIII-continued

| R | W | Bridge | R$_4$ | R$_5$ | Z | X | R$_a$ | R$_b$ | (m.p. °C.) |
|---|---|---|---|---|---|---|---|---|---|
| H | O | 2- | 3-SO$_2$N(CH$_3$)$_2$ | H | N | OCH$_3$ | CO$_2$CH$_3$ | F | |

TABLE IX

| R | W | Bridge | R$_4$ | R$_5$ | Y$_1$ | R$_a$ | R$_b$ | (m.p. °C.) |
|---|---|---|---|---|---|---|---|---|
| CH$_3$ | O | 2- | 3-SO$_2$CH$_2$CH$_3$ | H | CH$_3$ | CN | H | |
| H | S | 2- | 3-SCH$_2$CH$_3$ | H | CH$_3$ | CN | H | |
| H | O | 3- | 2-SO$_2$CH$_2$CH$_3$ | H | H | CN | F | |
| H | O | 3- | 2-SO$_2$N(CH$_3$)$_2$ | H | H | CN | OCH$_3$ | |
| H | O | 3- | 4-SO$_2$CH$_2$CH$_3$ | H | H | CN | SCH$_3$ | |
| H | O | 3- | 2-SO$_2$CH$_2$CH$_3$ | 4-SCH$_3$ | H | CN | H | |
| H | O | 3- | 2-SO$_2$CH$_2$CH$_3$ | 4-CO$_2$CH$_3$ | CH$_3$ | CO$_2$CH$_3$ | F | |
| H | O | 2- | 3-SCH$_2$CH$_3$ | H | CH$_3$ | CO$_2$CH$_3$ | OCH$_3$ | |
| H | O | 2- | 3-SO$_2$CH$_2$CH$_3$ | H | H | CO$_2$CH$_3$ | SCH$_3$ | |
| H | O | 2- | 3-SO$_2$N(CH$_3$)$_2$ | H | CH$_3$ | CO$_2$CH$_2$CH$_3$ | H | |
| H | O | 3- | 4-SO$_2$N(CH$_3$)$_2$ | H | CH$_3$ | CO$_2$CH$_3$ | F | |

TABLE X

| R | W | Bridge | R$_6$ | R$_7$ | Z | X | R$_a$ | R$_b$ | (m.p. °C.) |
|---|---|---|---|---|---|---|---|---|---|
| H | O | 2- | 3-CO$_2$CH$_3$ | H | CH | OCH$_3$ | CN | OCH$_3$ | |
| H | O | 2- | 3-CO$_2$CH$_3$ | H | CH | OCH$_3$ | CO$_2$CH$_3$ | H | 126–129 |
| H | O | 2- | 3-CO$_2$CH$_3$ | 6-OCH$_3$ | CH | OCH$_3$ | CN | SCH$_3$ | |
| H | O | 2- | 3-CO$_2$CH$_3$ | 6-CH$_3$ | CH | OCH$_3$ | CN | CH$_3$ | |
| H | O | 2- | 3-OCH$_2$CH$_3$ | H | CH | OCH$_3$ | CN | SCH$_3$ | |
| H | O | 2- | 3-OCH$_2$CH$_3$ | H | N | OCH$_3$ | CN | H | |
| H | O | 2- | 3-SCH$_2$CH$_3$ | H | CH | OCH$_3$ | CN | H | |
| H | O | 2- | 3-CON(CH$_3$)$_2$ | H | CH | OCH$_3$ | CN | H | |
| H | O | 2- | 3-CO$_2$CH$_3$ | H | CH | OCH$_3$ | CN | H | |
| H | O | 2- | 3-SO$_2$Et | H | CH | OCH$_3$ | CN | H | |
| H | O | 2- | 3-CH(CH$_3$)$_2$ | H | CH | OCH$_3$ | CN | H | |
| H | O | 2- | 3-CH$_2$CH$_3$ | H | N | OCH$_3$ | CN | F | |
| H | O | 2- | 3-L-1, R$_h$ = H | H | CH | OCH$_3$ | CO$_2$CH$_3$ | F | |
| H | O | 2- | 3-L-3 | H | CH | OCH$_3$ | CO$_2$CH$_3$ | OCH$_3$ | |
| H | O | 2- | 3-L-5 | H | CH | OCH$_3$ | CO$_2$CH$_3$ | CH$_3$ | |
| H | O | 2- | 3-L-26, R$_j$ = H | H | N | OCH$_3$ | CO$_2$CH$_3$ | F | |
| H | O | 3- | 2-CO$_2$CH$_3$ | H | CH | OCH$_3$ | CO$_2$CH$_3$ | H | |
| H | O | 3- | 2-SO$_2$CH$_2$CH$_3$ | H | CH | OCH$_3$ | CO$_2$CH$_3$ | OCH$_3$ | |
| H | O | 3- | 1-SO$_2$N(CH$_3$)$_2$ | H | CH | OCH$_3$ | CN | OCH$_3$ | |
| H | O | 3- | 1-SO$_2$CH$_2$CH$_3$ | H | N | OCH$_3$ | CO$_2$CH$_3$ | OCH$_3$ | |
| H | O | 3- | 2-Cl | H | N | OCH$_3$ | CN | F | |
| H | O | 3- | 1-OCH$_2$CH$_3$ | H | CH | OCH$_3$ | CO$_2$CH$_3$ | SCH$_3$ | |
| H | O | 3- | 2-COCH$_2$CH$_3$ | H | CH | OCH$_3$ | CN | OCH$_3$ | |
| H | O | 3- | 2-SCH$_2$CH$_3$ | H | N | OCH$_3$ | CO$_2$CH$_3$ | CH$_3$ | |
| H | O | 3- | 1-OCH$_2$CF$_3$ | H | CH | OCH$_3$ | CN | H | |
| H | O | 3- | 2-L-3 | H | CH | OCH$_3$ | CN | F | |

TABLE X-continued

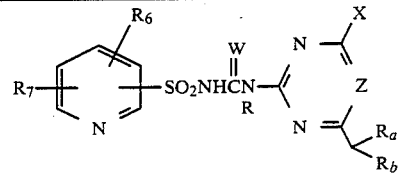

| R | W | Bridge | R6 | R7 | Z | X | Ra | Rb | (m.p. °C.) |
|---|---|---|---|---|---|---|---|---|---|
| H | O | 3- | 2-L-26, Rj = CH3 | H | CH | OCH3 | CO2CH3 | F | |
| H | O | 2- | 3-CH(OCH3)2 | H | CH | OCH3 | CN | H | |
| H | O | 2- | 3-C(CH3)(OCH3)2 | H | CH | OCH3 | CN | H | |

TABLE XI

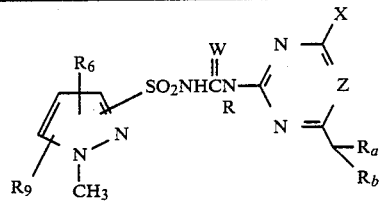

| R | W | Bridge | R6 | R9 | Z | X | Ra | Rb | (m.p. °C.) |
|---|---|---|---|---|---|---|---|---|---|
| H | O | 3- | 2-CH(OCH3)2 | H | CH | OCH3 | CO2CH3 | F | |
| H | O | 2- | 3-SO2CH2CH3 | H | CH | OCH3 | CO2CH3 | H | 125–130 |
| CH3 | O | 5- | 4-CO2CH3 | H | CH | OCH3 | CN | H | |
| H | S | 5- | 4-CO2CH3 | H | CH | OCH3 | CN | H | |
| H | O | 5- | 4-CO2CH3 | 3-Cl | CH | OCH3 | CN | H | |
| H | O | 5- | 4-Cl | H | CH | OCH3 | CN | F | |
| H | O | 5- | 4-COCH2CH3 | H | CH | OCH3 | CN | OCH3 | |
| H | O | 5- | 4-SO2CH2CH3 | H | CH | OCH3 | CN | H | |
| H | O | 5- | 4-SO2N(CH3)2 | H | CH | OCH3 | CO2CH3 | H | |
| H | O | 5- | 4-OCH2CH3 | H | CH | OCH3 | CN | H | |
| H | O | 5- | 4-CH(CH3)2 | H | CH | OCH3 | CO2CH3 | F | |
| H | O | 5- | 4-SCH2CH3 | H | N | OCH3 | CO2CH3 | H | |
| H | O | 5- | 4-L-26, Rj = CH3 | H | CH | OCH3 | CO2CH3 | H | |
| H | O | 4- | 5-CO2CH3 | H | CH | OCH3 | CO2CH3 | H | |
| H | O | 4- | 5-CO2CH3 | H | CH | OCH3 | CN | H | |
| H | O | 4- | 5-SO2CH2CH3 | H | CH | OCH3 | CO2CH3 | F | |
| H | O | 4- | 5-SO2N(CH3)2 | H | N | OCH3 | CO2CH3 | H | |
| H | O | 4- | 5-SO2CH2CH3 | 3-CH3 | CH | OCH3 | CO2CH3 | H | |
| H | O | 4- | 5-Cl | H | N | OCH3 | CO2CH3 | F | |
| H | O | 4- | 5-SCH2CH3 | H | CH | OCH3 | CN | OCH3 | |
| H | O | 4- | 3-SO2CH2CH3 | H | CH | OCH3 | CN | H | |
| H | O | 4- | 3-SO2N(CH3)2 | H | CH | OCH3 | CO2CH3 | OCH3 | |
| H | O | 4- | 3-CO2CH3 | 5-CH3 | CH | OCH3 | CN | H | |
| H | O | 4- | 3-SCH2CH3 | H | N | OCH3 | CO2CH3 | OCH3 | |
| H | O | 4- | 3-Cl | H | CH | OCH3 | CN | H | |
| H | O | 3- | 4-CO2CH3 | H | CH | OCH3 | CN | H | |
| H | O | 3- | 4-SO2CH2CH3 | H | CH | OCH3 | CO2CH3 | F | |
| H | O | 3- | 4-SO2N(CH3)2 | H | CH | OCH3 | CO2CH3 | OCH3 | |
| H | O | 3- | 4-COCH2CH3 | H | CH | OCH3 | CN | OCH3 | |
| H | O | 3- | 4-Cl | H | CH | OCH3 | CN | F | |
| H | O | 3- | 4-OCH2CH3 | H | CH | OCH3 | CN | H | |

TABLE XII

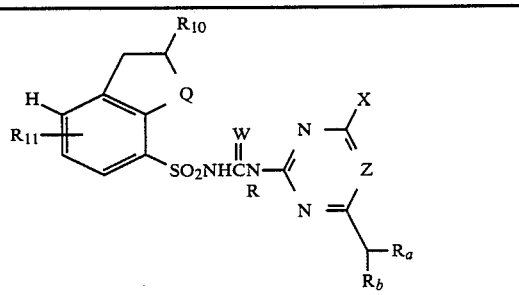

| R | W | Q | R10 | R11 | Z | X | Ra | Rb | (m.p. °C.) |
|---|---|---|---|---|---|---|---|---|---|
| CH3 | O | SO2 | CH3 | H | CH | OCH3 | CN | H | |

TABLE XII-continued

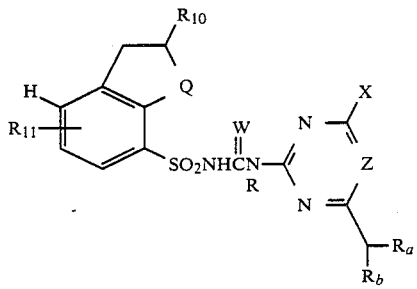

| R | W | Q | $R_{10}$ | $R_{11}$ | Z | X | $R_a$ | $R_b$ | (m.p. °C.) |
|---|---|---|---|---|---|---|---|---|---|
| H | S | $SO_2$ | $CH_3$ | H | CH | $OCH_3$ | CN | H | |
| H | O | $SO_2$ | $CH_3$ | H | CH | $OCH_3$ | CN | H | 200–205 |
| H | O | $SO_2$ | $CH_3$ | H | CH | $OCH_3$ | CN | F | |
| H | O | $SO_2$ | $CH_3$ | H | CH | $OCH_3$ | CN | $SCH_3$ | |
| H | O | $SO_2$ | $CH_3$ | H | CH | $OCH_3$ | CN | Cl | |
| H | O | $SO_2$ | $CH_3$ | H | $CH_3$ | $OCH_2CH_3$ | CN | H | 199–203 |
| H | O | $SO_2$ | $CH_3$ | H | CH | $OCH_3$ | CN | $CH_3$ | 113(d) |
| H | O | $SO_2$ | $CH_3$ | H | N | $OCH_3$ | CN | H | |
| H | O | $SO_2$ | $CH_3$ | H | CH | $OCH_3$ | $CO_2CH_3$ | H | |
| H | O | $SO_2$ | $CH_3$ | H | CH | $OCH_3$ | $CO_2CH_3$ | F | |
| H | O | $SO_2$ | $CH_3$ | H | CH | $OCH_3$ | $CO_2CH_3$ | $OCH_3$ | |
| H | O | $SO_2$ | $CH_3$ | H | CH | $OCH_3$ | $CO_2CH_3$ | H | 97(d) |
| H | O | $SO_2$ | $CH_3$ | H | CH | $OCH_3$ | $CO_2CH_2CH_3$ | F | |
| H | O | O | $CH_3$ | H | CH | $OCH_3$ | CN | H | |
| H | O | O | H | H | CH | $OCH_3$ | CN | F | |
| H | O | O | $CH_3$ | H | N | $OCH_3$ | $CO_2CH_3$ | H | |
| H | O | O | $CH_3$ | H | CH | $OCH_3$ | $CO_2CH_3$ | $OCH_3$ | |
| H | O | O | $CH_3$ | H | N | $OCH_3$ | $CO_2CH_3$ | $SCH_3$ | |
| H | O | CO | $CH_3$ | H | CH | $OCH_3$ | CN | H | |
| H | O | CO | $CH_3$ | H | CH | $OCH_3$ | $CO_2CH_3$ | H | |

TABLE XIII

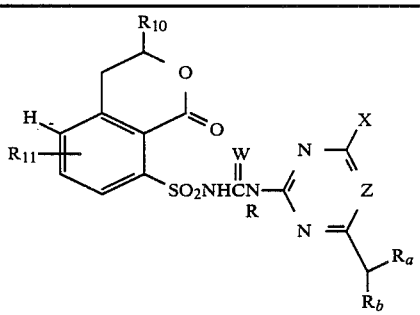

| R | W | $R_{10}$ | $R_{11}$ | Z | X | $R_a$ | $R_b$ | (m.p. °C.) |
|---|---|---|---|---|---|---|---|---|
| $CH_3$ | O | H | H | CH | $OCH_3$ | CN | H | |
| H | S | H | H | CH | $OCH_3$ | CN | H | |
| H | O | $CH_3$ | H | CH | $OCH_3$ | CN | H | 189–193 |
| H | O | H | H | CH | $OCH_3$ | CN | H | 171–176 |
| H | O | H | H | CH | $OCH_3$ | CN | $OCH_3$ | |
| H | O | H | H | CH | $OCH_3$ | CN | $SCH_3$ | |
| H | O | $CH_3$ | H | N | $OCH_3$ | CN | H | |
| H | O | H | H | N | $OCH_3$ | CN | F | |
| H | O | $CH_3$ | H | CH | $OCH_3$ | $CO_2CH_3$ | H | |
| H | O | H | H | CH | $OCH_3$ | $CO_2CH_3$ | H | 180–181 |
| H | O | H | H | CH | $OCH_3$ | $CO_2CH_3$ | $OCH_3$ | |
| H | O | $CH_3$ | H | CH | $OCH_3$ | $CO_2CH_3$ | H | |
| H | O | H | H | N | $OCH_3$ | $CO_2CH_2CH_3$ | H | |

TABLE XIV

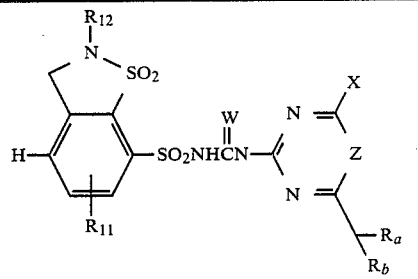

| R | W | $R_{12}$ | $R_{11}$ | Z | X | $R_a$ | $R_b$ | (m.p. °C.) |
|---|---|---|---|---|---|---|---|---|
| $CH_3$ | O | $CH_3$ | H | CH | $OCH_3$ | CN | H | |
| H | S | $CH_3$ | H | CH | $OCH_3$ | CN | H | |
| H | O | $CH_3$ | H | CH | $OCH_3$ | CN | H | |
| H | O | $CH_3$ | H | CH | $OCH_3$ | CN | F | |
| H | O | $CH_3$ | H | CH | $OCH_3$ | CN | $OCH_3$ | |
| H | O | $CH_3$ | H | CH | $OCH_3$ | CN | $SCH_3$ | |
| H | O | $CH_3$ | H | CH | $OCH_3$ | CN | $CH_3$ | |
| H | O | H | H | CH | $OCH_3$ | CN | F | |
| H | O | C(O)$CH_3$ | H | CH | $OCH_3$ | CN | $OCH_3$ | |
| H | O | $CH_3$ | H | CH | $OCH_3$ | $CO_2CH_3$ | H | |
| H | O | $CH_3$ | H | CH | $OCH_3$ | $CO_2CH_3$ | F | |
| H | O | $CH_3$ | H | CH | $OCH_3$ | $CO_2CH_3$ | $OCH_3$ | |
| H | O | $CH_3$ | H | CH | $OCH_3$ | $CO_2CH_3$ | $SCH_3$ | |
| H | O | $CH_3$ | H | CH | $OCH_3$ | $CO_2CH_3$ | $CH_3$ | |
| H | O | $CO_2CH_3$ | H | CH | $OCH_3$ | $CO_2CH_3$ | F | |
| H | O | $CH_2CH_2Cl$ | H | CH | $OCH_3$ | CN | H | |
| H | O | $CH_2CHF_2$ | H | CH | $OCH_3$ | CN | H | |
| H | O | $CH_2CH_3$ | H | CH | $OCH_3$ | CN | H | |
| H | O | $CH_2CH_2F$ | H | CH | $OCH_3$ | $CO_2CH_3$ | H | 168–169 |
| H | O | $(CH_2)_3CH_3$ | H | CH | $OCH_3$ | $CO_2CH_3$ | H | 173–174 |
| H | O | $(CH_2)_2CH_3$ | H | CH | $OCH_3$ | $CO_2CH_3$ | H | 176– |

TABLE XIV-continued

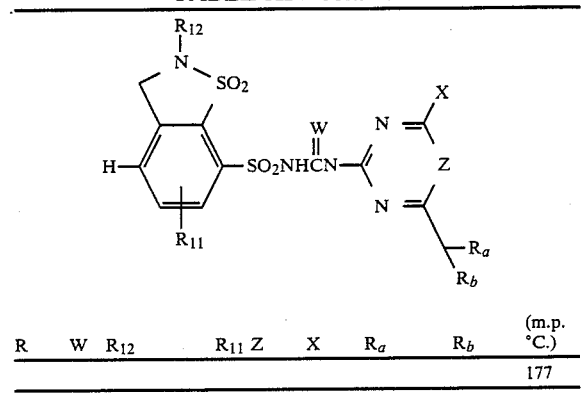

| R | W | R12 | R11 | Z | X | Ra | Rb | (m.p. °C.) |
|---|---|---|---|---|---|---|---|---|
| | | | | | | | | 177 |

TABLE XV

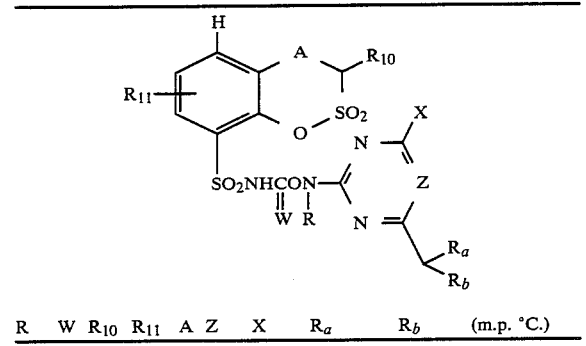

| R | W | R10 | R11 | A | Z | X | Ra | Rb | (m.p. °C.) |
|---|---|---|---|---|---|---|---|---|---|
| CH3 | O | CH3 | H | db | CH | OCH3 | CN | H | |
| H | S | CH3 | H | db | CH | OCH3 | CN | H | |
| H | O | CH3 | H | sb | CH | OCH3 | CN | H | |
| H | O | CH3 | H | db | CH | OCH3 | CN | F | |
| H | O | CH3 | H | db | CH | OCH3 | CN | OCH3 | |
| H | O | CH3 | H | db | CH | OCH3 | CN | SCH3 | |
| H | O | CH3 | H | db | CH | OCH3 | CN | CH3 | |
| H | O | CH3 | H | sb | CH | OCH3 | CO2CH3 | H | |
| H | O | CH3 | H | sb | CH | OCH3 | CO2CH3 | F | |
| H | O | CH3 | H | sb | CH | OCH3 | CO2CH3 | OCH3 | |
| H | O | CH3 | H | sb | CH | OCH3 | CO2CH3 | SCH3 | |

TABLE XV-continued

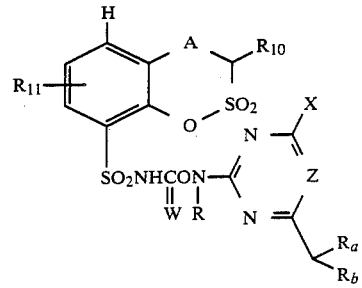

| R | W | R10 | R11 | A | Z | X | Ra | Rb | (m.p. °C.) |
|---|---|---|---|---|---|---|---|---|---|
| H | O | CH3 | H | sb | N | OCH3 | CO2CH3 | SCH3 | | for A:
db = double bond
sb = single bond

TABLE XVI

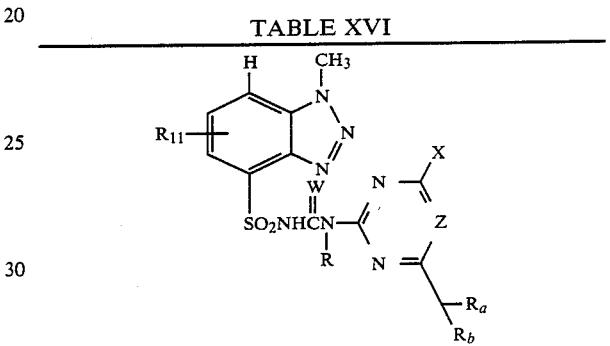

| R | W | R11 | Z | X | Ra | Rb | (m.p. °C.) |
|---|---|---|---|---|---|---|---|
| CH3 | O | H | CH | OCH3 | CN | H | |
| H | S | H | CH | OCH3 | CN | H | |
| H | O | H | CH | OCH3 | CN | F | |
| H | O | H | CH | OCH3 | CN | OCH3 | |
| H | O | H | N | OCH3 | CN | OCH3 | |
| H | O | H | N | OCH3 | CN | F | |
| H | O | H | CH | OCH3 | CH2CH3 | F | |
| H | O | H | CH | OCH3 | CH2CH3 | OCH3 | |
| H | O | H | CH | OCH3 | CH2CH3 | SCH3 | |
| H | O | H | CH | OCH3 | CO2CH3 | H | |

TABLE XVII

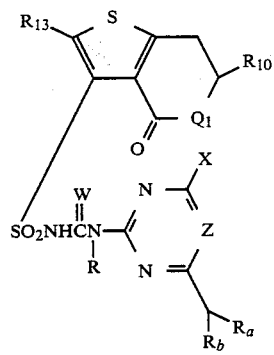

| R | W | R13 | R10 | Q1 | Z | X | Ra | Rb | (m.p. °C.) |
|---|---|---|---|---|---|---|---|---|---|
| CH3 | O | H | CH3 | O | CH | OCH3 | CN | H | |
| H | S | H | CH3 | O | CH | OCH3 | CN | F | |
| H | O | H | H | O | CH | OCH3 | CN | OCH3 | |
| H | O | H | H | O | CH | OCH3 | CN | SCH3 | |
| H | O | H | H | O | N | OCH3 | CN | F | |
| H | O | H | H | NCH3 | CH | OCH3 | CN | F | |
| H | O | H | H | NCH2CH3 | CH | OCH3 | CN | H | |

TABLE XVII-continued

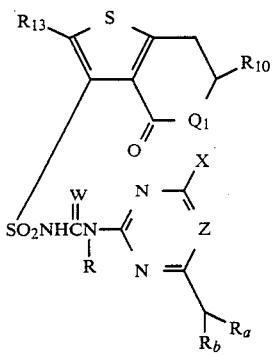

| R | W | R13 | R10 | Q1 | Z | X | Ra | Rb | (m.p. °C.) |
|---|---|---|---|---|---|---|---|---|---|
| H | O | H | H | O | CH | OCH3 | CO2CH3 | F | |
| H | O | H | H | O | CH | OCH3 | CO2CH3 | OCH3 | |
| H | O | H | H | O | CH | OCH3 | CO2CH3 | SCH3 | |
| H | O | H | H | NCH3 | CH | OCH3 | CO2CH3 | SCH3 | |
| H | O | H | H | O | N | OCH3 | CO2CH3 | SCH3 | |

TABLE XVIII

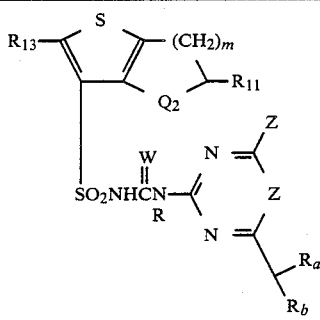

| R | W | m | R11 | R13 | Q2 | Z | X | Ra | Rb | (m.p. °C.) |
|---|---|---|---|---|---|---|---|---|---|---|
| CH3 | O | 1 | CH3 | H | SO2 | CH | OCH3 | CN | H | |
| H | S | 1 | CH3 | H | SO2 | CH | OCH3 | CN | H | |
| H | O | 1 | CH3 | H | SO2 | N | OCH3 | CN | F | |
| H | O | 1 | CH3 | H | SO2 | CH | OCH3 | CN | OCH3 | |
| H | O | 1 | CH3 | H | SO2 | CH | OCH3 | CN | SCH3 | |
| H | O | 1 | CH3 | H | SO2 | CH | OCH3 | CN | F | |
| H | O | 1 | CH3 | H | SO2 | CH | OCH3 | CO2CH3 | H | |
| H | O | 2 | CH3 | H | SO2 | CH | OCH3 | CO2CH3 | F | |
| H | O | 1 | CH3 | H | SO2 | CH | OCH3 | CO2CH3 | OCH3 | |
| H | O | 1 | CH3 | H | SO2 | CH | OCH3 | CO2CH3 | SCH3 | |
| H | O | 1 | CH3 | H | SO2 | N | OCH3 | CO2CH3 | F | |

TABLE XIX

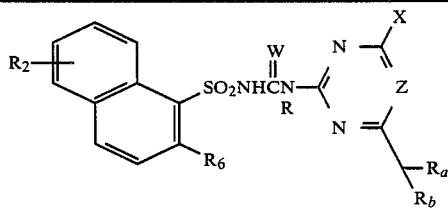

| R | W | R2 | R6 | Z | X | Ra | Rb | (m.p. °C.) |
|---|---|---|---|---|---|---|---|---|
| CH3 | O | H | Cl | CH | OCH3 | CN | H | |
| H | S | H | Cl | CH | OCH3 | CN | H | |
| H | O | H | Cl | CH | OCH3 | CN | H | 195–196 |
| H | O | H | CO2CH3 | CH | OCH3 | CN | F | |
| H | O | H | CO2CH3 | CH | OCH3 | CN | OCH3 | |
| H | O | H | CO2CH3 | CH | OCH3 | CN | SCH3 | |
| H | O | H | CO2CH3 | N | OCH3 | CN | F | |
| H | O | H | CO2CH3 | N | OCH3 | CN | OCH3 | |

TABLE XIX-continued

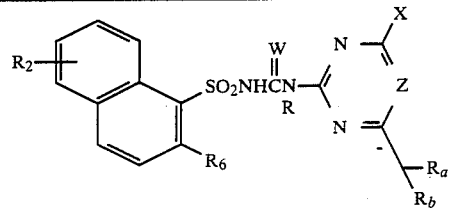

| R | W | $R_2$ | $R_6$ | Z | X | $R_a$ | $R_b$ | (m.p. °C.) |
|---|---|---|---|---|---|---|---|---|
| H | O | H | Cl | N | $OCH_3$ | $CO_2CH_3$ | H | |
| H | O | H | Cl | N | $OCH_3$ | $CO_2CH_3$ | F | |
| H | O | H | Cl | N | $OCH_3$ | $CO_2CH_3$ | $OCH_3$ | |
| H | O | H | $SO_2CH_2CH_3$ | N | $OCH_3$ | $CO_2CH_3$ | $OCH_3$ | |
| H | O | H | $SO_2N(CH_3)_2$ | N | $OCH_3$ | $CO_2CH_3$ | H | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

| | Active Ingredient | Weight Percent* | |
|---|---|---|---|
| | | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications Oxford, 1968, pp. 101-103.

In the following examples, all parts are by weight unless otherwise indicated.

EXAMPLE 5

Wettable Powder

2-[[[4-(Cyanomethyl)-6-methoxypyrimidin-2-yl]aminocarbonyl]aminosulfonyl]-4-(2,2,2-trifluoroethoxy)-benzoic acid, methyl ester, 80%
sodium alkylnaphthalenesulfonate, 2%
sodium ligninsulfonate, 2%
synthetic amorphous silica, 3%
kaolinite, 13%

The ingredients are blended, hammer-milled until all the solids are essentially under 50 microns, reblended, and packaged.

EXAMPLE 6

Wettable Powder

N-[[4-(Cyanomethyl)-6-methoxypyrimidin-2-yl]aminocarbonyl]-3,4-dihydro-1-oxo-1H-2-benzopyran-8-sulfonamide, 50%
sodium alkylnaphthalenesulfonate, 2%
low viscosity methyl cellulose, 2%
diatomaceous earth, 46%

The ingredients are blended, coarsely hammer-milled and then air-milled to produce particles essentially all below 10 microns in diameter. The product is reblended before packaging.

EXAMPLE 7

Granule

Wettable Powder of Example 6, 5%
attapulgite granules, 95%
(U.S.S. 20–40 mesh; 0.84–0.42 mm)

A slurry of wettable powder containing 25% solids is sprayed on the surface of attapulgite granules in a double-cone blender. The granules are dried and packaged.

EXAMPLE 8

Extruded Pellet

2-[[(2,3-Dihydro-2-methylbenzo[b]thiophen-7-yl)-sulfonylamino]carbonylamino]-6-methoxy-4-pyrimidineacetic acid, methyl ester, S,S-dioxide, 25%
anhydrous sodium sulfate, 10%
crude calcium ligninsulfonate, 5%
sodium alkylnaphthalenesulfonate, 1%
calcium/magnesium bentonite, 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

Low Strength Granule

2-[[[4-(Cyanomethyl)-6-methoxypyrimidin-2-yl]aminocarbonyl]aminosulfonyl]-4-(2,2,2-trifluoroethoxy)-benzoic acid, methyl ester, 1%
N,N-dimethylformamide, 9%
attapulgite granules, 90%
(U.S.S. 20 to 40 sieve)

The active ingredient is dissolved in the solvent and the solution is sprayed upon dedusted granules in a double-cone blender. After spraying of the solution has been completed, the blender is allowed to run for a short period and then the granules are packaged.

EXAMPLE 10

Granule

N-[[4-(Cyanomethyl)-6-methoxypyrimidin-2-yl]aminocarbonyl]-3,4-dihydro-1-oxo-1H-2-benzopyran-8-sulfonamide, 80%
wetting agent 1%
crude ligninsulfonate salt (containing 5–20% of the natural sugars) 10%
attapulgite clay, 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then dscharged, screened to the desired size range, generally 14–100 mesh (1410–149 microns), and packaged for use.

EXAMPLE 11

Low Strength Granule

2-[[(2,3-Dihydro-2-methylbenzo[b]thiophen-7-yl)sulfonylamino]carbonylamino]-6-methoxy-4-pyrimidineacetic acid, methyl ester, S,S-dioxide, 1%
N,N-dimethylformamide, 9%
attapulgite granules 90%
(U.S.S. 20 to 40 sieve)

The active ingredient is dissolved in the solvent and the solution is sprayed upon dedusted granules in a double cone blender. After spraying of the solution has been completed, the blender is allowed to run for a short period and then the granules are packaged.

EXAMPLE 12

Aqueous Suspension

2-[[[4-(Cyanomethyl)-6-methoxypyrimidin-2-yl]aminocarbonyl]aminosulfonyl]-4-(2,2,2-trifluoroethoxy)-benzoic acid, methyl ester, 40%
polyacrylic acid thickener 0.3%
dodecylphenol polyethylene glycol ether 0.5%
disodium phosphate 1%
monosodium phosphate 0.5%
polyvinyl alcohol 1.0%
water 56.7%

The ingredients are blended and ground together in a sand mill to produce particles essentially all under 5 microns in size.

EXAMPLE 13

Solution

N-[[4-(Cyanomethyl)-6-methoxypyrimidin-2-yl]aminocarbonyl]-3,4-dihydro-1-oxo-1H-2-benzopyran-8-sulfonamide, ammonium salt, 5%
water, 95%

The salt is added directly to the water with stirring to produce the solution, which may then be packaged for use.

EXAMPLE 14

High Strength Concentrate

2-[[(2,3-Dihydro-2-methylbenzo[b]thiophen-7-yl)sulfonylamino]carbonylamino]-6-methoxy-4-pyrimidineacetic acid, methyl ester, S,S-dioxide, 99%
silica aerogel, 0.5%
synthetic amorphous silica, 0.5%

The ingredients are blended and ground in a hammer-mill to produce a material essentially all passing a U.S.S. No. 50 screen (0.3 mm opening). The concentrate may be formulated further if necessary.

EXAMPLE 15

Wettable Powder

2-[[[4-(Cyanomethyl)-6-methoxypyrimidin-2-yl]aminocarbonyl]aminosulfonyl]-4-(2,2,2-trifluoroethoxy)-benzoic acid, methyl ester, 90%
dioctyl sodium sulfosuccinate 0.1%
synthetic fine silica 9.9%

The ingredients are blended and ground in a hammer-mill to produce particles essentially all below 100 microns. The material is sifted through a U.S.S. No. 50 screen and then packaged.

EXAMPLE 16

Wettable Powder

N-[[4-(Cyanomethyl)-6-methoxypyrimidin-2-yl]aminocarbonyl]-3,4-dihydro-1-oxo-1H-2-benzopyran-8-sulfonamide, 40%
sodium ligninsulfonate, 20%
montmorillonite clay, 40%

The ingredients are thoroughly blended, coarsely hammer-milled and then air-milled to produce particles essentially all below 10 microns in size. The material is reblended and then packaged.

EXAMPLE 17

Oil Suspension

2-[[(2,3-Dihydro-2-methylbenzo[b]thiophen-7-yl)sulfonylamino]carbonylamino]-6-methoxy-4-pyrimidineacetic acid, methyl ester, S,S-dioxide, 35%
blend of polyalcohol carboxylic esters and oil soluble petroleum sulfonates 6%
xylene, 59%

The ingredients are combined and ground together in a sand mill to produce particles essentially all below 5 microns. The product can be used directly, extended with oils, or emulsified in water.

EXAMPLE 18

Dust

2-[[[4-(Cyanomethyl)-6-methoxypyrimidin-2-yl]aminocarbonyl]aminosulfonyl]-4-(2,2,2-trifluoroethoxy)-benzoic acid, methyl ester, 10%
attapulgite, 10%
Pyrophyllite, 80%

The active ingredient is blended with attapulgite and then passed through a hammer-mill to produce particles substantially all below 200 microns. The ground concentrate is then blended with powdered pyrophyllite until homogeneous.

EXAMPLE 19

Oil Suspension

N-[[4-(Cyanomethyl)-6-methoxypyrimidin-2-yl]aminocarbonyl]-3,4-dihydro-1-oxo-1H-2-benzopyran-8-sulfonamide, 25%
polyoxyethylene sorbitol hexaoleate 5%
highly aliphatic hydrocarbon oil 70%

The ingredients are ground together in a sand mill until the solid particles have been reduced to under about 5 microns. The resulting thick suspension may be applied directly, but preferably after being extended with oils or emulsified in water.

Utility

Test results indicate that the compounds of the present invention are highly active preemergent or postemergent herbicides or plant growth regulants. Many of them have utility for broad-spectrum pre- and or post-emergence weed control in areas where complete control of all vegetation is desired, such as around fuel storage tanks, industrial storage areas, parking lots, drive-in theaters, around billboards, highway and railroad structures. Some of the compounds have utility for selective weed control in crops such as wheat, barley, rice, corn and cotton. Alternatively, the subject compounds are useful to modity plant growth.

The rate of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 5 kg/ha, the lower rates being suggested for use on lighter soils and/or those having a low organic matter content, for selective weed control or for situations where only short-term persistence is required, such as a herbicide for fallow land.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

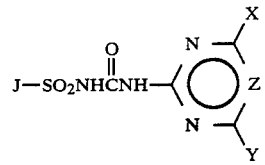

| Compound | X | J is | Y | Z |
|---|---|---|---|---|
| 1 | OCH₃ | (CF₃CH₂O-benzene-CO₂CH₃) | CH₂CN | CH |

-continued
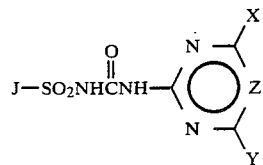
| | | | |
|---|---|---|---|
| 2 | OCH₃ | CH₂CN | CH |
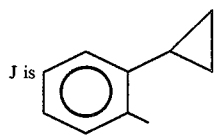
| | | | |
|---|---|---|---|
| 3 | OCH₃ | CH₂CN | CH |
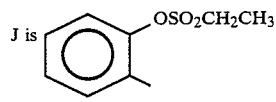
| | | | |
|---|---|---|---|
| 4 | OCH₃ | CH₂CN | CH |
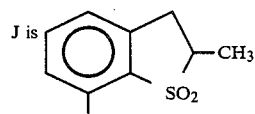
| | | | |
|---|---|---|---|
| 5 | OCH₂CH₃ | CH₂CN | CH |
| 6 | OCH₃ | CH(CH₃)CN | CH |
| 7 | OCH₃ | CH₂CO₂CH₃ | CH |
| 8 | OCH₃ | CH₂CN | CH |
| 9 | CH₃ | CH₂CN | CH |
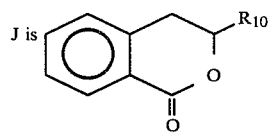
| Compound | R₁₀ | X | Y | Z |
|---|---|---|---|---|
| 10 | CH₃ | OCH₃ | CH₂CN | CH |
| 11 | H | OCH₃ | CH₂CN | CH |
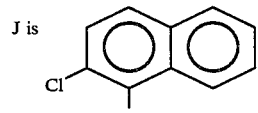
| | | | |
|---|---|---|---|
| 12 | OCH₃ | CH₂CN | CH |
| Compound | J | X | Y | Z |
|---|---|---|---|---|
| 13 |  | OCH₃ | CH₂CO₂CH₃ | CH |

-continued

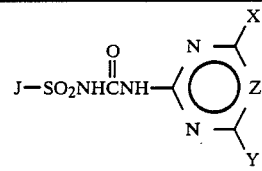

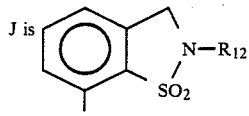

| Compound | R_{12} | X | Y | Z |
|---|---|---|---|---|
| 14 | $(CH_2)_3CH_3$ | $OCH_3$ | $CH_2CO_2CH_3$ | CH |
| 15 | $(CH_2)_2CH_3$ | $OCH_3$ | $CH_2CO_2CH_3$ | CH |
| 16 | $CH_2CH_2F$ | $OCH_3$ | $CH_2CO_2CH_3$ | CH |
| 17 | isochromanone | $OCH_3$ | $CH_2CO_2CH_3$ | CH |
| 18 | (methyl tetrazolyl)methylphenyl | $OCH_3$ | $CH_2CO_2CH_3$ | CH |
| 19 | 2-methyl-3-(ethylsulfonyl)pyridyl | $OCH_3$ | $CH_2CO_2CH_3$ | CH |
| 20 | 2-methyl-3-(methoxycarbonyl)pyridyl | $OCH_3$ | $CH_2CO_2CH_3$ | CH |
| 21 | 4-(difluoromethoxy)-2-methyl-(ethoxycarbonyl)phenyl | $OCH_3$ | $CH_2CO_2CH_3$ | CH |
| 22 | 4-(trifluoroethoxy)-2-methyl-(methoxycarbonyl)phenyl | $OCH_3$ | $CH_2CO_2CH_3$ | CH |

Test A

Seeds of crabgrass (Digitaria sp.), barnyard-grass (Echinochloa crus-galli), giant foxtail (Setaria faberi), wild oats (Avena fatua), velvetleaf (Abutilon theophrasti), morningglory (Ipomoea spp.), cocklebur (Xanthium pensylvanicum), sorghum, corn, soybean, surgarbeet, cotton, rice, wheat, barley and purple nutsedge (Cyperus rotundus) tubers and optionally cheatgrass (Bromus secalinus) and downy brome (Bromus tectorum) were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, whereupon all species were compared to controls and visually rate for response to treatment. The ratings are based on a numerical scale extending from 0=no injury, to 10=complete kill. The accompanying descriptive symbols have the following meanings:

C=chlorosis or necrosis;
B=burn
D=defoliation
E=emergence inhibition;
G=growth retardation;
H=formative effects;
U=unusual pigmentation
X=axillary stimulation; and
S=albinism
6Y=abscised buds or flowers.

TABLE A

| RATE = KG/HA | CMPD 1 0.05 | CMPD 1 0.01 | CMPD 2 0.05 | CMPD 2 0.01 | CMPD 3 0.05 | CMPD 3 0.01 | CMPD 4 0.05 | CMPD 4 0.01 | CMPD 5 0.05 | CMPD 5 0.01 | CMPD 6 0.05 | CMPD 6 0.01 | CMPD 7 0.05 | CMPD 7 0.01 | CMPD 8 0.05 | CMPD 8 0.01 | CMPD 9 0.05 | CMPD 9 0.01 | CMPD 10 0.05 | CMPD 10 0.01 | CMPD 11 0.05 | CMPD 11 0.01 |
|---|---|---|---|---|---|---|---|---|---|---|---|---|---|---|---|---|---|---|---|---|---|---|
| POSTEMERGENCE ||||||||||||||||||||||
| COTTON | 2G | 0 | 4C,9G | 3G | 3C,8G | 5G | 5G | 0 | 0 | 0 | 0 | 0 | 4C,9G | 4C,9G | 3G | 2C,2H | 0 | 0 | 7G | 0 | 5C,9G | 2C,8G |
| MORNINGLRY | 5C,9G | 3C,7G | 3C,9G | 3C,5G | 3C,8G | 2G | 4C,8H | 3H | 4C,8H | 0 | 0 | 0 | 10C | 3C,8G | 3C,8H | 3C,7G | 0 | 0 | 9C | 3C,8G | 10C | 4C,9G |
| COCKLEBUR | 4C,9G | 3C,9G | 3C,9G | 4C,9G | 2C,8G | 2C,5G | 5C,9G | 2C,8G | 2C,5H | 0 | 3G | 3G | 4C,9H | 3H | 3C,8H | 2C,2H | 0 | 0 | 10C | 4C,9G | 10C | 4C,9G |
| NUTSEDGE | 10C | 0 | 0 | 0 | 4C,8G | 0 | 0 | 0 | 0 | — | 0 | 0 | 3C,7G | 2C,5G | 0 | 0 | 0 | 0 | 3C,7G | 0 | 2C,4G | 0 |
| CRABGRASS | 2C,5G | 0 | 2G | 0 | 7G | 0 | 4G | 0 | 2C,5G | 2G | 0 | 3G | 9C | 4C,9G | 9C | 9C | 0 | 0 | 9C | 4G | 4C,9G | 3C,8G |
| BARNYARDGRASS | 4C,9G | 3C,8H | 3C,9H | 2C,7G | 3C,9H | 3C,9H | 4C,9H | 0 | 3C,7H | 0 | 4H | 0 | 9C | 5C,9H | 5C,9G | 5C,9H | 0 | 0 | 5C,9G | 3C,8H | 10C | 5C,9H |
| WILD OATS | 3C,6G | 2C,5G | 3C,6G | 0 | 2C,5G | 2C,2G | 2G | 0 | 3C,9G | 2C,6G | 3C,7G | 2G | 4C,8G | 2C,4G | 3C,9G | 3C,9G | 0 | 0 | 2C,8G | 3G | 3C,8G | 3C,6G |
| WHEAT | 2C,9G | 8G | 5G | 0 | 5G | 2G | 3G | 0 | 7G | 3G | 3C,7H 5G | 2G | 3C,9G | 4C,9G | 3C,9G | 2C,9G | 0 | 0 | 2C,9G | 2C,8G | 9G | 2C,9G |
| CORN | 4C,9G | 2C,6G | 3C,8H | 2C,4G | 4C,9G | 4C,9G | 3C,5H | 2G | 9G | 3G | 3C,7G 3C,5G | 0 | 9C | 3C,9G | 5C,9G | 9C | 0 | 0 | 10C | 3C,9G | 9C | 9C |
| SOYBEANS | 3C,9G | 3C,7H | 4C,9G | 3C,8G | 4C,9G | 3C,8G | 3C,9H | 2C,8G | 3C,6H | 2H | 3C,7H | 1H | 5C,9G | 3C,8G | 4C,8H | 3C,5H | 0 | 0 | 4C,9G | 3C,9G | 5C,9G | 5C,9G |
| RICE | 3C,9G | 3C,6G | 3G | 1C | 2C,7G | 4G | 4G | 0 | 3G | 0 | 3C,5G | 0 | 9C | 2C,7G | 5C,9G | 7G | 0 | 0 | 4C,9G | 3C,9G | 5C,9G | 5C,9G |
| SORGHUM | 4C,9G | 4C,9G | 3C,8H | 3C,8H | 4C,9G | 9G | 4C,9G | 2C,8G | 8G | 4G | 3C,7G | 2G | 5C,9G | 3C,9H | 4C,8G | 3C,8G | 0 | 0 | 3C,9G | 3C,8G | 9C | 4C,9H |
| CHEAT GRASS | 9C | 6G | 6G | 3G | 6G | 6G | — | — | 8G | 4G | — | — | — | — | 9C 3C,7G | 5C,9G 3C,7G | 0 | 0 | — | — | — | — |
| SUGARBEET | 9C | 9C | 9C | 3C,8H | 9C | 9C | 4C,9H | 7G | 4C,7H | 2C,4G | 4C,9G | 3G | 10C | 4C,8G | | | 0 | 0 | 4C,9G | 0 | 9C | 10C |
| VELVETLEAF | 7G | 3G | 3C,7G | 5G | 3C,7G | 5G | 0 | 0 | 0 | 0 | 3G | 2G | 5C,9H | 0 | 3C,7H | 5H | 0 | 0 | 4C,8G | 5G | 5C,9G | 2C,5G |
| GIANT FOXTAIL | 5C,9G | 3C,6G | 4C,8G | 2G | 3C,8G | 2C, 4G | 3C,8H | 0 | 2C,6G | 4G | 3G | 2G | 9C | 3C,8G | 9C | 3C,8H | 0 | 0 | 9C | 3C,9G | 9C | 3C,8G |
| BARLEY | 3C,9G | 3C,9G | 3C,9G | 4G | 3C,8G | 3C, 8G | 3C,8G | 0 | 8G | 4G | 3C,8G | 3C,7G | 5C,9G | 3C,8G | 5C,9G | 5C,9G | 0 | 0 | 4C,9G | 3C,8G | 5C,9G | 4C,9G |
| DOWNY BROME | — | — | — | — | — | — | — | — | — | — | 5G | 0 | 4C,9G | 2C,5G | — | — | — | — | 7G | 2G | 3C,6G | 3C,7G |
| PREEMERGENCE ||||||||||||||||||||||
| COTTON | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| MORNINGLRY | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| COCKLEBUR | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| NUTSEDGE | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| CRABGRASS | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| BARNYARDGRASS | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| WILD OATS | 0 | 0 | 0 | 0 | 0 | 0 | 0 | 0 | 0 | 0 | 0 | 0 | 2G | 0 | 0 | 0 | 0 | 0 | 0 | 0 | 0 | 0 |
| WHEAT | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| CORN | 0 | 0 | 0 | 0 | 0 | 0 | 0 | 0 | 0 | 0 | 0 | 0 | 2G | 0 | 0 | 0 | 0 | 0 | 0 | 0 | 0 | 0 |
| SOYBEANS | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| RICE | 0 | 0 | 0 | 0 | 0 | 0 | 0 | 0 | 0 | 0 | 0 | 0 | 2G | 0 | 0 | 0 | 0 | 0 | 0 | 0 | 0 | 0 |
| SORGHUM | 0 | 0 | 0 | 0 | 0 | 0 | 0 | — | 0 | 0 | 0 | 0 | — | 0 | 0 | 0 | 0 | — | 0 | — | — | — |
| CHEAT GRASS | 0 | 0 | 0 | 0 | 0 | 0 | 0 | 0 | 0 | 0 | 0 | 0 | 2H | 0 | 0 | 0 | 2H | 0 | 0 | 0 | 0 | 0 |
| SUGARBEET | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| VELVETLEAF | 0 | 0 | 0 | 0 | 0 | 0 | 0 | 0 | 0 | 0 | 0 | 0 | 3G | 0 | 0 | 0 | 0 | 0 | 0 | 0 | 0 | 0 |
| GIANT FOXTAIL | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| BARLEY | 0 | 0 | 0 | 0 | 0 | 0 | 0 | 0 | 0 | 0 | 0 | 0 | 2G | 0 | 0 | 0 | 0 | 0 | 0 | 0 | 0 | 0 |
| DOWNY BROME | — | — | — | — | — | — | — | — | — | — | — | — | — | — | — | — | — | — | — | — | — | — |

TABLE A-continued

| RATE = KG/HA | CMPD 12 | | CMPD 13 | | CMPD 14 | | CMPD 15 | | CMPD 16 | | CMPD 17 | | CMPD 18 | | CMPD 19 | | CMPD 20 | | CMPD 21 | | CMPD 22 | |
|---|---|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | | | |
| COTTON | 5G | 0 | 4C,9G | 7G | 0 | 0 | 3C,7H | 0 | 3C,8H | 2C | 4C,8H | 8G | 5C,9G | 3C,8G | 0 | 0 | 2C,7G | 0 | 3C,9G | 3C,9G | 5C,9G | 0 |
| MORNINGLRY | 2C,5G | 0 | 9C | 1C | 0 | 0 | 3C,7G | 0 | 3C,7G | 0 | 10C | 3C,9G | 9C | 4C,8H | 0 | 0 | 0 | 0 | 9C | 3C,7G | 9C | 4C,9G |
| COCKLEBUR | 2C,8G | 2C,5H | 4C,9G | 3H | 0 | 0 | 0 | 0 | 0 | 0 | 10C | 3C,9H | 3G | 0 | 0 | 0 | 0 | 0 | 5C,9G | 4C,8G | 5C,9G | 3C,6G |
| NUTSEDGE | 0 | 0 | 0 | 0 | 0 | 0 | 0 | 0 | 0 | 0 | 7G | 0 | 5G | 0 | 0 | 0 | 0 | 0 | 6C,9G | 2G | 0 | 0 |
| CRABGRASS | 0 | 0 | 0 | 0 | 0 | 0 | 3C,8G | 0 | 3C,7G | 0 | 9C | 3G | 5C,9G | 3H | 0 | 0 | 0 | 0 | 5G | 2G | 2G | 0 |
| BARNYARDGRASS | 1H | 0 | 4C,9H | 7H | 2G | 0 | 4C,9G | 3C,6H | 4C,9H | 3C,5G | 4C,9G | 3C,9G | 3G | 0 | 0 | 0 | 0 | 0 | 5C,9H | 2C,4H | 3C,9G | 6G |
| WILD OATS | 0 | 0 | 0 | 0 | 0 | 0 | 3C,7G | 2G | 2C,4G | 0 | 3C,6G | 4G | 5C,9G | 0 | 0 | 0 | 0 | 0 | 4G | 0 | 2G | 0 |
| WHEAT | 0 | 0 | 0 | 0 | 0 | 0 | 9G | 6G | 9G | 8G | 3C,8G | 3C,9H | 0 | 3G | 0 | 0 | 0 | 0 | 3C,8G | 2C,4H | 3C,9G | 2C,2G |
| CORN | 2C,5G | 2G | 3C,8H | 0 | 2C,2H | 0 | 3C,9G | 1H | 3C,7H | 2C,2H | 9C | 3C,9H | 5C,9G | 3C,7G | 0 | 0 | 0 | 0 | 4C,9G | 4C,9G | 3C,9G | 3C,7G |
| SOYBEANS | 2C,7G | 2G | 4C,9G | 3C,7G | 0 | 0 | 3C,7G | 1H | 3C,8G | 3C,4G | 4C,9H | 3C,8G | 3C,6G | 0 | 0 | 0 | 2C,6H | 0 | 2C,2G | 3C,9G | 3C,7G | 2G |
| RICE | 0 | 0 | 2C,3G | 2G | 0 | 0 | 2C,3G | 0 | 0 | 0 | 9C | 0 | 4C,9G | 3C,7H | 0 | 0 | 0 | 0 | 5C,9G | 0 | 8G | 0 |
| SORGHUM | 3C,9G | 3C,7G | 3C,9G | 3C,8G | 0 | 0 | 3C,7G | 2G | 3C,5H | 2G | 5C,9G | 4C,9G | 4C,9G | 3G | 3G | 0 | 0 | 0 | 4G | 3C,9G | 4G | 2G |
| CHEAT GRASS | 0 | 0 | 7G | 2G | 2C | 0 | 7G | 0 | 5G | 2G | 5C,9G | 7G | 4C,9G | 3C,5H | 0 | 0 | 2C,6G | 0 | 8G | 0 | 8G | 0 |
| SUGARBEET | 3C,8G | 3C,8G | 9C | 4C,9G | 0 | 0 | 3C,7H | 4G | 3C,8H | 3G | 10C | 4C,9G | 9C | 0 | 0 | 0 | 0 | 0 | 9C | 3C,7G | 9C | 2G |
| VELVETLEAF | 3G | 3G | 0 | 7G | 2G | 0 | 0 | 0 | 0 | 0 | 9C | 7G | 4C,8H | 3C,9G | 0 | 0 | 0 | 0 | 5C,9G | 3G | 4C,9G | 2G |
| GIANT FOXTAIL | 0 | 0 | 2C,5G | 0 | 2G | 0 | 5C,9G | 6G | 5C,9G | 3C,7G | 4C,9G | 4G | 5C,9G | 3G | 0 | 0 | 0 | 0 | 3C,7G | 5G | 3C,9G | 2C,5G |
| BARLEY | 2G | 0 | 4G | 0 | 0 | 0 | 9G | 3G | 3C,9G | 5G | 5C,9G | 6G | 3C,9G | 5G | 0 | 0 | 0 | 0 | 8G | 0 | 9G | 8G |
| DOWNY BROME | — | — | | | | | | | | | | | | | | | | | | | | |
| PREEMERGENCE | | | | | | | | | | | | | | | | | | | | | | |
| COTTON | 0 | 0 | 0 | 0 | 0 | 0 | 0 | 0 | 0 | 0 | 0 | 0 | 0 | 0 | 0 | 0 | 0 | 0 | 1C | 0 | 0 | 0 |
| MORNINGLRY | 0 | 0 | 0 | 0 | 0 | 0 | 0 | 0 | 2G | 0 | 0 | 0 | 0 | 0 | 0 | 0 | 0 | 0 | 1C | 0 | 0 | 0 |
| COCKLEBUR | 0 | 0 | 3H | 0 | 0 | 0 | 0 | 0 | 0 | 0 | 0 | 0 | 0 | 0 | 0 | 0 | 0 | 0 | 3C | 0 | 0 | 0 |
| NUTSEDGE | 0 | 0 | 0 | 0 | 0 | 0 | 0 | 0 | 0 | 0 | — | 0 | 0 | 0 | 0 | 0 | 0 | 0 | 4G | 0 | 0 | 0 |
| CRABGRASS | 0 | 0 | 0 | 0 | 0 | 0 | 0 | 0 | 0 | 0 | 0 | 0 | 0 | 0 | 0 | 0 | 0 | 0 | 0 | 0 | 2G | 0 |
| BARNYARDGRASS | 0 | 0 | 0 | 0 | 0 | 0 | 0 | 0 | 0 | 0 | 0 | 0 | 0 | 0 | 0 | 0 | 0 | 0 | 2G | 0 | 0 | 0 |
| WILD OATS | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| WHEAT | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| CORN | 0 | 0 | 0 | 0 | 0 | 0 | 0 | 0 | 0 | 0 | 2G | 0 | 0 | 0 | 0 | 0 | 0 | 0 | 0 | 0 | 2C,2G | 0 |
| SOYBEANS | 0 | 0 | 0 | 0 | 0 | 0 | 0 | 0 | 0 | 0 | 0 | 0 | 0 | 0 | 0 | 0 | 0 | 0 | 2C | 0 | 2C | 0 |
| RICE | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| SORGHUM | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| CHEAT GRASS | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| SUGARBEET | 0 | 0 | 0 | 0 | 0 | 0 | 0 | 0 | 0 | 0 | 0 | 0 | 0 | 0 | 0 | 0 | 0 | 0 | 8G | 0 | 0 | 0 |
| VELVETLEAF | 0 | 0 | 0 | 0 | 0 | 0 | 0 | 0 | 0 | 0 | 0 | 0 | 0 | 0 | 0 | 0 | 0 | 0 | 0 | 0 | 2G | 0 |
| GIANT FOXTAIL | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| BARLEY | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| DOWNY BROME | — | — | | | | | | | | | | | | | | | | | | | | |

Test B

Postemergence

Three round pans (25 cm diameter by 122.5 cm deep) were filled with Sassafrass sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and prickly sida (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*), and giant foxtail (*Setaria faberi*). The third pot was planted with wheat (*Tricticum aestivum*), barley (*Hordeum vulgare*), wild buckwheat (*Polygonum convolvulus* L.), downy brome (*Bromus tectorum*), sugarbeet (*Beta vulgaris*), wild oat (*Avena fatua* L.), common chickweed (*Stellaria media*), blackgrass (*Alopercurus myosuroides*), and rape (*Brassica napus*). The plants were grown for approximately fourteen days, then sprayed postemergence with the chemicals dissoled in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvtleaf, lambsquarters, rice, and teaweed. The second pot was planted with green foxtail, cocklebur, morningglory, cotton, johnsongrass, barnyardgrass, corn, soybean, and giant foxtail. The third pot was planted with wheat, barley, wild buckwheat, cheatgrass, surgarbeet, wild oat, viola, blackgrass, and rape. The three pans were sprayed preemergence with the chemicals dissolved in a non-phytotoxic solvent.

Treated plants and controls were maintained in the greenhouse for approximately 24 days, then all rated plants were compared to controls and visually rated for plant response.

Response ratings are based on a scale of 0 to 100 where 0=no effect, and 100=complete control. A dash (-) response means no test.

Response ratings are contained in Table B.

TABLE B

| RATE = G/HA | CMPD 8 | | | |
|---|---|---|---|---|
| | 0125 | 0062 | 0016 | 0004 |
| POSTEMERGENCE | | | | |
| GIANT FOXTAIL | 30 | 10 | 0 | 0 |
| VELVETLEAF | 90 | 80 | 40 | 40 |
| SUGARBEET | 90 | 70 | 40 | — |
| CRABGRASS | — | 40 | 20 | 0 |
| PRICKLY SIDA | 40 | — | 20 | 0 |
| JIMSONWEED | 70 | — | 40 | 0 |
| RICE | 0 | 0 | 0 | 0 |
| COCKLEBUR | 70 | 60 | 40 | 0 |
| COTTON | 0 | 0 | 0 | 0 |
| SOYBEANS | 0 | 0 | 0 | 0 |
| BARNYARDGRASS | 0 | 0 | 0 | 0 |
| WILD OATS | 40 | 30 | 30 | 20 |
| IVY MORNINGLORY | 40 | 30 | 0 | 0 |
| WHEAT | 10 | 0 | 0 | 0 |
| SICKLEPOD | 0 | — | — | 0 |
| JOHNSONGRASS | 60 | 20 | — | — |
| PURPLE NUTSEDGE | 0 | 0 | 0 | 0 |
| CORN | 0 | 0 | 0 | 0 |
| WILD BUCKWHEAT | 100 | 90 | 20 | — |
| BLACKGRASS | 80 | 70 | 50 | 30 |
| RAPE | 80 | 80 | 40 | 20 |
| BARLEY | 0 | 0 | 0 | 0 |
| GREEN FOXTAIL | 80 | 70 | 30 | 0 |
| CHICKWEED | 90 | 80 | 40 | 0 |
| DOWNY BROME | 40 | 10 | 0 | 0 |

TABLE B-continued

| RATE = G/HA | CMPD 8 | |
|---|---|---|
| | 0125 | 0062 |
| PREEMERGENCE | | |
| GIANT FOXTAIL | 0 | 0 |
| VELVETLEAF | 70 | 50 |
| SUGARBEET | 40 | 10 |
| CRABGRASS | 10 | 0 |
| PRICKLY SIDA | 40 | 0 |
| JIMSONWEED | 0 | 0 |
| RICE | 0 | 0 |
| COCKLEBUR | 0 | 0 |
| COTTON | 0 | 0 |
| SOYBEANS | 30 | 10 |
| BARNYARDGRASS | 0 | 0 |
| WILD OATS | 0 | 0 |
| IVY MORNINGLORY | 50 | 40 |
| WHEAT | 0 | 0 |
| SICKLEPOD | 20 | 0 |
| JOHNSONGRASS | 40 | 30 |
| PURPLE NUTSEDGE | — | 40 |
| CORN | 20 | 10 |
| WILD BUCKWHEAT | 40 | 0 |
| BLACKGRASS | 0 | 0 |
| RAPE | 10 | 0 |
| BARLEY | 20 | 10 |
| GREEN FOXTAIL | 10 | 0 |
| LAMBSQUARTER | 60 | 20 |
| CHICKWEED | 20 | — |
| DOWNY BROME | 40 | 10 |

What is claimed:

1. A compound selected from

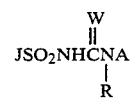

wherein

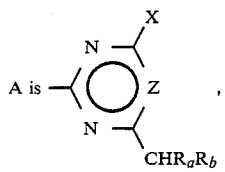

W is O or S;
R is H or CH$_3$;
R$_a$ is —CN or —CO$_2$R$_c$;
R$_b$ is H, CH$_3$, F, Cl, Br, OCH$_3$ or SCH$_3$;
R$_c$ is C$_1$-C$_4$ alkyl, C$_2$-C$_4$ haloalkyl, C$_3$-C$_4$ alkenyl, C$_3$-C$_4$ alkynyl or C$_2$-C$_4$ haloalkenyl;
X is H, CH$_3$, CH$_2$CH$_3$, C$_1$-C$_4$ alkoxy, SCH$_3$, C$_1$-C$_2$ haloalkoxy, SCF$_2$H or CH$_2$OCH$_3$;
Z is CH;
J is

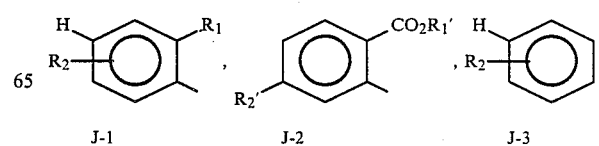

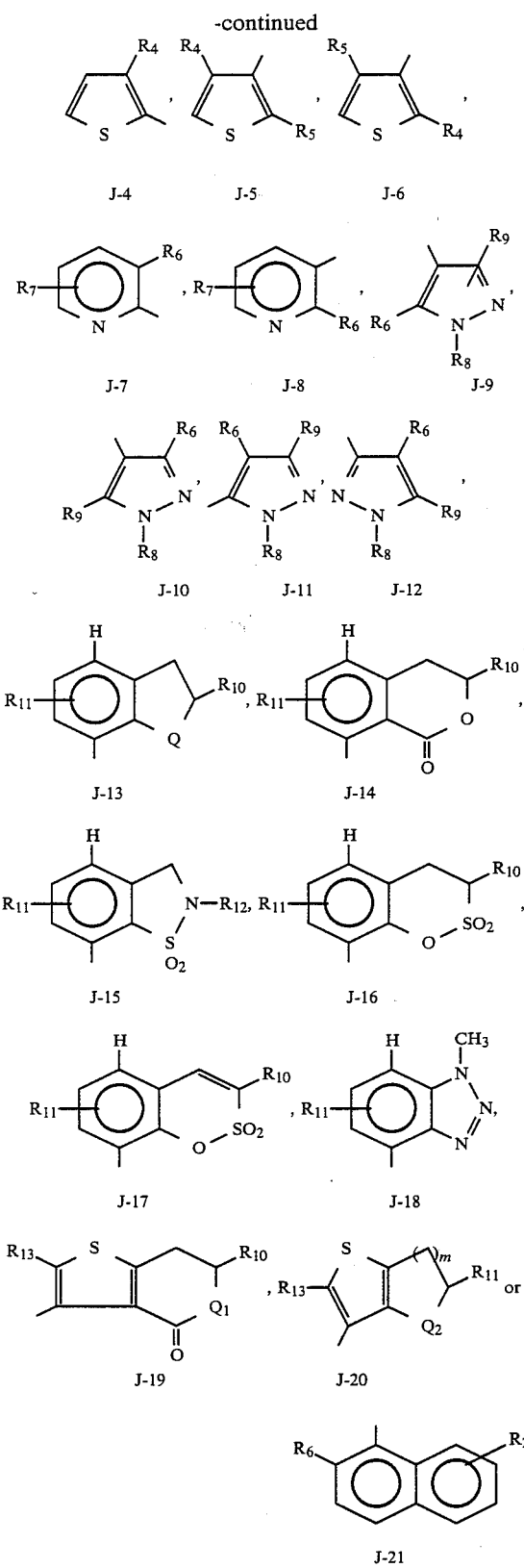

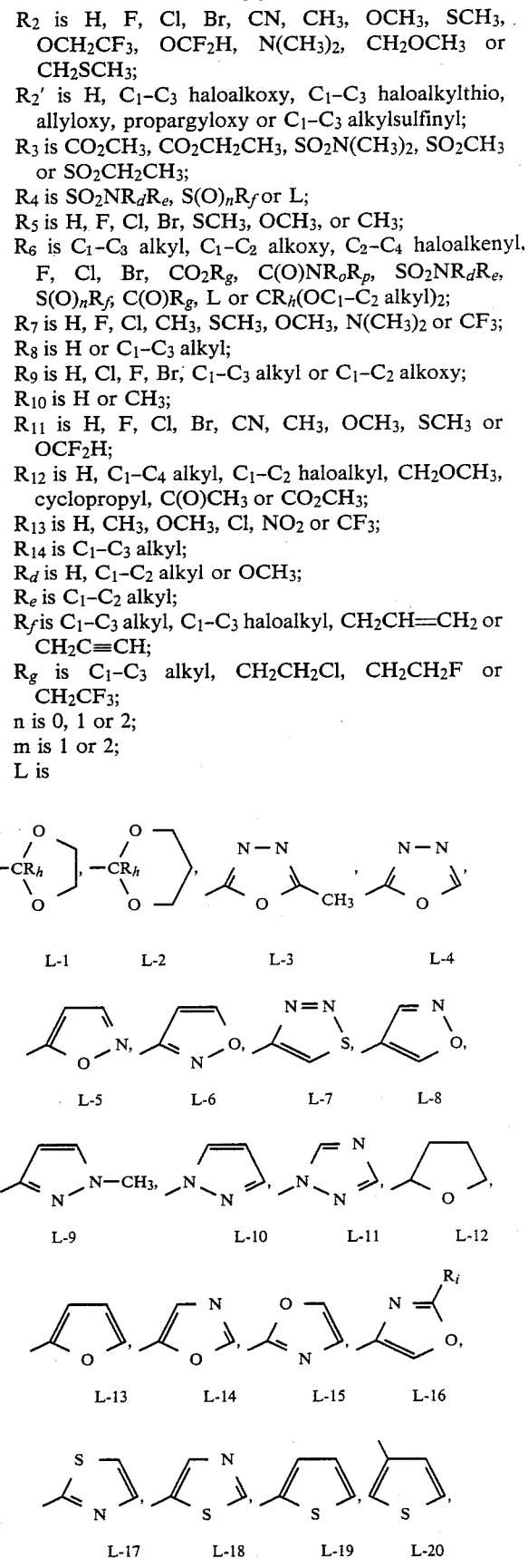

$R_1$ is $OS(O)_2R_{14}$ or L;
$R_1'$ is $C_1$-$C_3$ alkyl, $CH_2CH_2Cl$, $CH_2CH_2F$, $CH_2CF_3$ or $CH_2CH_2OCH_3$;
$R_2$ is H, F, Cl, Br, CN, $CH_3$, $OCH_3$, $SCH_3$, $OCH_2CF_3$, $OCF_2H$, $N(CH_3)_2$, $CH_2OCH_3$ or $CH_2SCH_3$;
$R_2'$ is H, $C_1$-$C_3$ haloalkoxy, $C_1$-$C_3$ haloalkylthio, allyloxy, propargyloxy or $C_1$-$C_3$ alkylsulfinyl;
$R_3$ is $CO_2CH_3$, $CO_2CH_2CH_3$, $SO_2N(CH_3)_2$, $SO_2CH_3$ or $SO_2CH_2CH_3$;
$R_4$ is $SO_2NR_dR_e$, $S(O)_nR_f$ or L;
$R_5$ is H, F, Cl, Br, $SCH_3$, $OCH_3$, or $CH_3$;
$R_6$ is $C_1$-$C_3$ alkyl, $C_1$-$C_2$ alkoxy, $C_2$-$C_4$ haloalkenyl, F, Cl, Br, $CO_2R_g$, $C(O)NR_oR_p$, $SO_2NR_dR_e$, $S(O)_nR_f$, $C(O)R_g$, L or $CR_h(OC_1$-$C_2$ alkyl$)_2$;
$R_7$ is H, F, Cl, $CH_3$, $SCH_3$, $OCH_3$, $N(CH_3)_2$ or $CF_3$;
$R_8$ is H or $C_1$-$C_3$ alkyl;
$R_9$ is H, Cl, F, Br, $C_1$-$C_3$ alkyl or $C_1$-$C_2$ alkoxy;
$R_{10}$ is H or $CH_3$;
$R_{11}$ is H, F, Cl, Br, CN, $CH_3$, $OCH_3$, $SCH_3$ or $OCF_2H$;
$R_{12}$ is H, $C_1$-$C_4$ alkyl, $C_1$-$C_2$ haloalkyl, $CH_2OCH_3$, cyclopropyl, $C(O)CH_3$ or $CO_2CH_3$;
$R_{13}$ is H, $CH_3$, $OCH_3$, Cl, $NO_2$ or $CF_3$;
$R_{14}$ is $C_1$-$C_3$ alkyl;
$R_d$ is H, $C_1$-$C_2$ alkyl or $OCH_3$;
$R_e$ is $C_1$-$C_2$ alkyl;
$R_f$ is $C_1$-$C_3$ alkyl, $C_1$-$C_3$ haloalkyl, $CH_2CH=CH_2$ or $CH_2C\equiv CH$;
$R_g$ is $C_1$-$C_3$ alkyl, $CH_2CH_2Cl$, $CH_2CH_2F$ or $CH_2CF_3$;
n is 0, 1 or 2;
m is 1 or 2;
L is -continued

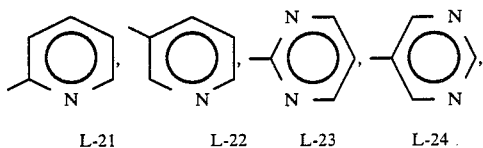

L-21   L-22   L-23   L-24

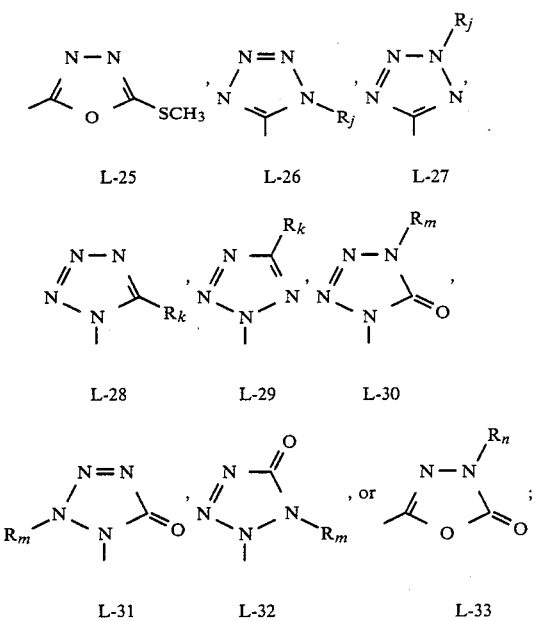

L-25   L-26   L-27

L-28   L-29   L-30

L-31   L-32   L-33

$R_h$ is H or $CH_3$;
$R_i$ is H or $CH_3$;
$R_j$ is H, $CH_3$ or $CH_2CH_3$;
$R_k$ is H, $CH_3$, $CH_2CH_3$, $OCH_3$, $OCH_2CH_3$, $SCH_3$ or $SCH_2CH_3$;
$R_m$ is H, $CH_3$ or $CH_2CH_3$;
$R_n$ is H or $CH_3$;
$R_o$ is H, $C_1-C_2$ alkyl or $OCH_3$;
$R_p$ is $C_1-C_2$ alkyl;
$R_q$ is $C_1-C_4$ alkyl, $C_1-C_4$ haloalkyl or cyclopropyl optionally substituted by halogen;
Q is O, S, SO, $SO_2$ or C(O);
$Q_1$ is O, $NCH_3$ or $NCH_2CH_3$;
$Q_2$ is S, SO or $SO_2$;
and their agriculturally suitable salts; provided that
(a) when J is J-1, then L is L-3 through L-33; and
(b) when $R_2'$ is H, then $R_b$ is F, Cl, Br, $OCH_3$ or $SCH_3$.

2. Compounds of claim 1 wherein W is O.
3. Compounds of claim 2 wherein $R_c$ is $CH_3$, $CH_2CH_3$, $C_3-C_4$ alkenyl or $C_3-C_4$ alkynyl.
4. Compounds of claim 3 wherein L is L-1, L-3, L-4, L-5, L-26, L-28 or L-30.
5. Compounds of claim 4 wherein J is J-1.
6. Compounds of claim 4 wherein J is J-2.
7. Compounds of claim 4 wherein J is J-3.
8. Compounds of calim 4 wherein J is J-4.
9. Compounds of claim 4 wherein J is J-5.
10. Compounds of claim 4 wherein J is J-6.
11. Compounds of claim 4 wherein J is J-7.
12. Compounds of claim 4 wherein J is J-8.
13. Compounds of claim 4 wherein J is J-9.
14. Compounds of claim 4 wherein J is J-10.
15. Compounds of claim 4 wherein J is J-11.
16. Compounds of claim 4 wherein J is J-12.
17. Compounds of claim 4 wherein J is J-13.
18. Compounds of claim 4 wherein J is J-14.
19. Compounds of claim 4 wherein J is J-15.
20. Compounds of claim 4 wherein J is J-16.
21. Compounds of claim 4 wherein J is J-17.
22. Compounds of claim 4 wherein J is J-18.
23. Compounds of claim 4 wherein J is J-19.
24. Compounds of claim 4 wherein J is J-20.
25. Compounds of claim 4 wherein J is J-21.
26. The compound of claim 1 which is 2-[[[4-(Cyanomethyl)-6-methoxypyrimidin-2-yl]aminocarobonyl]aminosulfonyl]-4-(2,2,2-trifluoroethoxy)benzoic acid, methyl ester.
27. The compound of claim 1 which is N-[[4-(Cyanomethyl)-6-methoxypyrimidin-2-yl]aminocarbonyl]-3,4-dihydro-1-oxo-1H-2-benzopyran-8-sulfonamide.
28. The compound of claim 1 which is 2-[[(2,3-Dihydro-2-methylbenzo[b]thiophen-7-yl)sulfonylamino]carbonylamino]-6-methoxy-4-pyrimidineacetic acid, methyl ester, S,S-dioxide.
29. A composition suitable for controlling the growth of undesired vegetation which comprises an effective amount of a compound of claim 1 and at least one of the following: surfactant, solid or liquid diluent.
30. A composition suitable for controlling the growth of undesired vegetation which comprises an effective amount of a compound of claim 2 and at least one of the following: surfactant, solid or liquid diluent.
31. A composition suitable for controlling the growth of undesired vegetation which comprises and effective amount of a compound of claim 3 and at least one of the following: surfactant, solid or liquid diluent.
32. A composition suitable for controlling the growth of undesired vegetation which comprises an effective amount of a compound of claim 4 and at least one of the following: surfactant, solid or liquid diluent.
33. A composition suitable for controlling the growth of undesired vegetation which comprises an effective amount of a compound of claim 5 and at least one of the following: surfactant, solid or liquid diluent.
34. A composition suitable for controlling the growth of undesired vegetation which comprises an effective amount of a compound of claim 6 and at least one of the following: surfactant, solid or liquid diluent.
35. A composition suitable for controlling the growth of undesired vegetation which comprises an effective amount of a compound of claim 7 and at least one of the following: surfactant, solid or liquid diluent.
36. A composition suitable for controlling the growth of undesired vegetation which comprises an effective amount of a compound of claim 8 and at least one of the following: surfactant, solid or liquid diluent.
37. A composition suitable for controlling the growth of undesired vegetation which comprises an effective amount of a compound of claim 9 and at least one of the following: surfactant, solid or liquid diluent.
38. A composition suitable for controlling the growth of undesired vegetation which comprises an effective amount of a compound of claim 10 and at least one of the following: surfactant, solid or liquid diluent.
39. A composition suitable for controlling the growth of undesired vegetation which comprises an effective amount of a compound of claim 11 and at least one of the following: surfactant, solid or liquid diluent.
40. A composition suitable for controlling the growth of undesired vegetation which comprises an effective amount of a compound of claim 12 and at least one of the following: surfactant, solid or liquid diluent.

41. A method for controlling the growth of undesired vegetation which comprises applying to the locus to be protected an effective amount of a compound of claim 1.

42. A method for controlling the growth of undesired vegetation which comprises applying to the locus to be protected an effective amount of a compound of claim 2.

43. A method for controlling the growth of undesired vegetation which comprises applying to the locus to be protected an effective amount of a compound of claim 3.

44. A method for controlling the growth of undesired vegetation which comprises applying to the locus to be protected an effective amount of a compound of claim 4.

45. A method for controlling the growth of undesired vegetation which comprises applying to the locus to be protected an effective amount of a compound of claim 5.

46. A method for controlling the growth of undesired vegetation which comprises applying to the locus to be protected an effective amount of a compound of claim 6.

47. A method for controlling the growth of undesired vegtation which comprises applying to the locus to be protected an effective amount of a compound of claim 7.

48. A method for controlling the growth of undesired vegetation which comprises applying to the locus to be protected an effective amount of a compound of claim 8.

49. A method for controlling the growth of undesired vegetation which comprises applying to the locus to be protected an effective amount of a compound of claim 9.

50. A method for controlling the growth of undesired vegetation which comprises applying to the locus to be protected an effective amount of a compound of claim 10.

51. A method for controlling the growth of undesired vegetation which comprises applying to the locus to be protected an effective amount of a compound of claim 11.

52. A method for controlling the growth of undesired vegetation which comprises applying to the locus to be protected an effective amount of a compound of claim 12.

53. A compound selected from

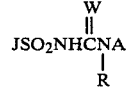

wherein

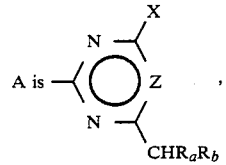    A-1

W is O or S;

R is H or $CH_3$;

$R_a$ is —CN or —$CO_2R_c$;

$R_b$ is H, $CH_3$, F, Cl, Br, $OCH_3$ or $SCH_3$;

$R_c$ is $C_1$-$C_4$ alkyl, $C_2$-$C_4$ haloalkyl, $C_3$-$C_4$ alkenyl, $C_3$-$C_4$ alkynyl or $C_2$-$C_4$ haloalkenyl;

X is H, $CH_3$, $CH_2CH_3$, $C_1$-$C_4$ alkoxy, $SCH_3$, $C_1$-$C_2$ haloalkoxy, $SCF_2H$ or $CH_2OCH_3$;

Z is CH;

J is

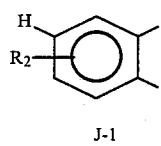 , 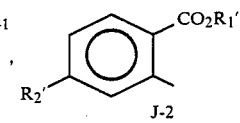

J-1    J-2

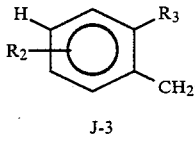 , 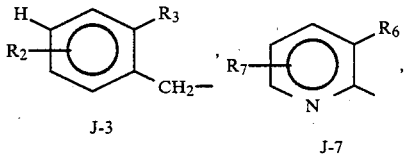

J-3    J-7

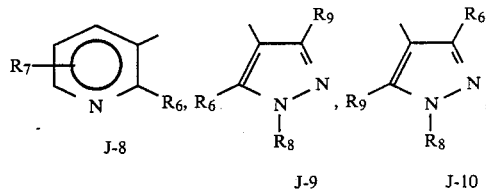

J-8    J-9    J-10

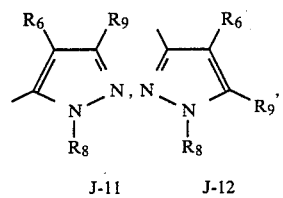

J-11    J-12

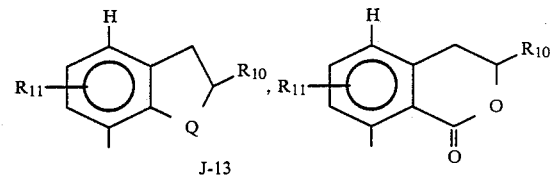

J-13    J-14

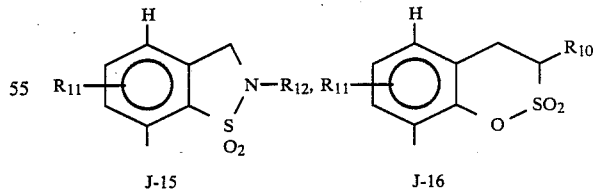

J-15    J-16

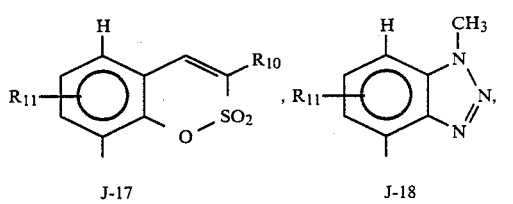

J-17    J-18

-continued

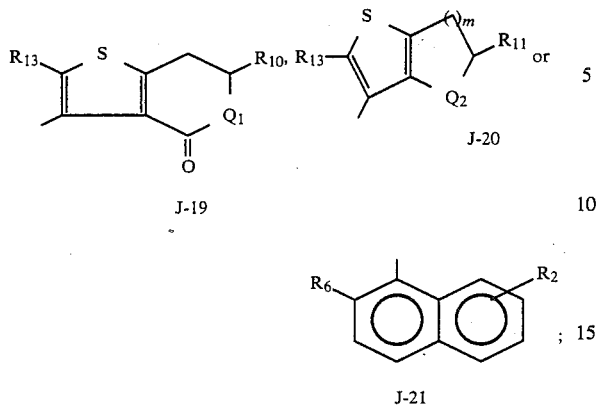

r₁ is $OS(O)_2R_{14}$ or L;
$R_1'$ is $C_1$-$C_3$ alkyl, $CH_2CH_2Cl$, $CH_2CH_2F$, $CH_2CF_3$ or $CH_2CH_2OCH_3$;
$R_2$ is H, F, Cl, Br, CN, $CH_3$, $OCH_3$, $SCH_3$, $OCH_2CF_3$, $OCF_2H$, $N(CH_3)_2$, $CH_2OCH_3$ or $CH_2SCH_3$;
$R_2'$ is H, $C_1$-$C_3$ haloalkoxy, $C_1$-$C_3$ haloalkylthio, allyloxy, propargyloxy or $C_1$-$C_3$ alkylsulfinyl;
$R_3$ is $CO_2CH_3$, $CO_2CH_2CH_3$, $SO_2N(CH_3)_2$, $SO_2CH_3$ or $SO_2CH_2CH_3$;
$R_6$ is $C_1$-$C_3$ alkyl, $C_1$-$C_2$ alkoxy, $C_2$-$C_4$ haloalkenyl, F, Cl, Br, $CO_2R_g$, $C(O)NR_oR_p$, $SO_2NR_dR_e$, $S(O)_nR_f$, $C(O)R_q$, L or $CR_h(OC_1$-$C_2$ alkyl$)_2$;
$R_7$ is H, F, Cl, $CH_3$, $SCH_3$, $OCH_3$, $N(CH_3)_2$ or $CF_3$;
$R_8$ is H or $C_1$-$C_3$ alkyl;
$R_9$ is H, Cl, F, Br, $C_1$-$C_3$ alkyl or $C_1$-$C_2$ alkoxy;
$R_{10}$ is H or $CH_3$;
$R_{11}$ is H, F, Cl, Br, CN, $CH_3$, $OCH_3$, $SCH_3$ or $OCF_2H$;
$R_{12}$ is H, $C_1$-$C_4$ alkyl, $C_1$-$C_2$ haloalkyl, $CH_2OCH_3$, cyclopropyl, $C(O)CH_3$ or $CO_2CH_3$;
$R_{13}$ is H, $CH_3$, $OCH_3$, Cl, $NO_2$ or $CF_3$;
$R_{14}$ is $C_1$-$C_3$ alkyl;
$R_d$ is H, $C_1$-$C_2$ alkyl or $OCH_3$;
$R_e$ is $C_1$-$C_2$ alkyl;
$R_f$ is $C_1$-$C_3$ alkyl, $C_1$-$C_3$ haloalkyl, $CH_2CH=CH_2$ or $CH_2C\equiv CH$;
$R_g$ is $C_1$-$C_3$ alkyl, $CH_2CH_2Cl$, $CH_2CH_2F$ or $CH_2CF_3$;
n is 0, 1 or 2;
m is 1 or 2;
L is

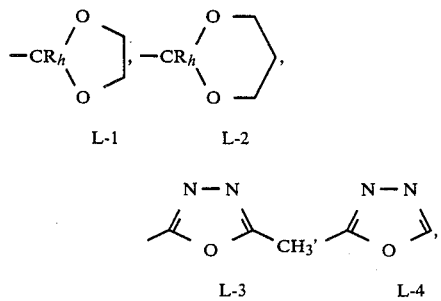

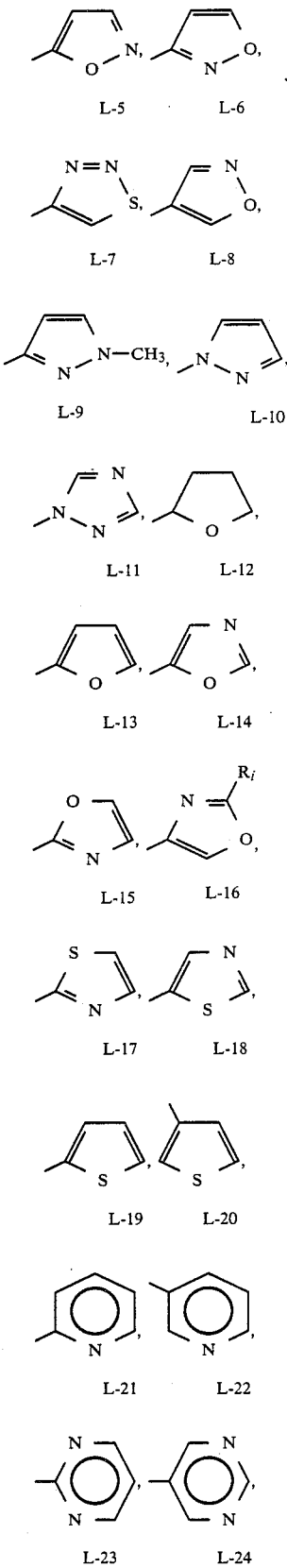

-continued

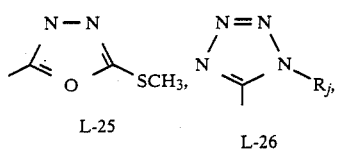

L-25, L-26

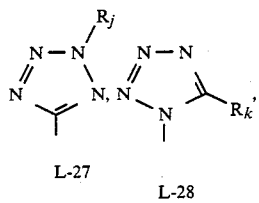

L-27, L-28

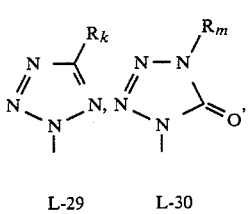

L-29, L-30

-continued

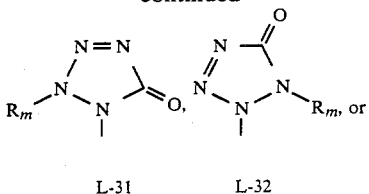

L-31, L-32, L-33

$R_h$ is H or CH3;
$R_i$ is H or CH3;
$R_j$ is H, CH3 or CH2CH3;
$R_k$ is H, CH3, CH2CH3, OCH3, OCH2CH3, SCH3 or SCH2CH3;
$R_m$ is H, CH3 or CH2CH3;
$R_n$ is H or CH3;
$R_o$ is H, $C_1$–$C_2$ alkyl or OCH3;
$R_p$ is $C_1$–$C_2$ alkyl;
$R_q$ is $C_1$–$C_4$ alkyl, $C_1$$C_4$ haloalkyl or cyclopropyl optionally substituted by halogen;
Q is O, S, SO, SO2 or C(O);
$Q_1$ is O, NCH3 or NCH2CH3;
$Q_2$ is S, SO or SO2;
and their agriculturally suitable salts; provided that
a. when J is J-1, then L is L-3 through L-33; and
b. when $R_2'$ is H, then $R_b$ is F, Cl, Br, OCH3 or SCH3.

* * * * *

UNITED STATES PATENT AND TRADEMARK OFFICE
CERTIFICATE OF CORRECTION

PATENT NO. : 4,844,727
DATED : July 4, 1989
INVENTOR(S) : Thomas Robert Dean

It is certified that error appears in the above-identified patent and that said Letters Patent is hereby corrected as shown below:

Column 48, lines 62 - 70, " 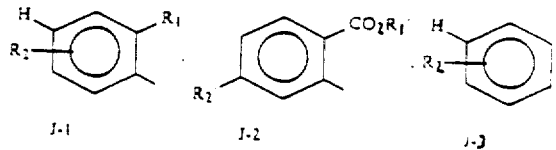 "

should read -- 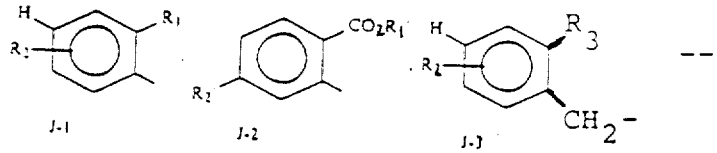 --

Column 55, line 20 "$r_1$" should read --$R_1$--.

Column 58, line 26 "$C_1C_4$" should read --$C_1-C_4$--.

Signed and Sealed this

Fourteenth Day of July, 1992

Attest:

DOUGLAS B. COMER

Attesting Officer

Acting Commissioner of Patents and Trademarks